US010765366B2

(12) United States Patent
Adachi et al.

(10) Patent No.: US 10,765,366 B2
(45) Date of Patent: Sep. 8, 2020

(54) APPLIANCE

(71) Applicant: OMRON HEALTHCARE Co., Ltd., Kyoto (JP)

(72) Inventors: Yuma Adachi, Kyoto (JP); Kengo Nishiyama, Kyoto (JP); Hiroshi Koshimizu, Kyoto (JP); Yoshihide Tokko, Kyoto (JP); Yuka Tanabe, Kyoto (JP); Kenji Ono, Kyoto (JP); Ryosuke Doi, Kyoto (JP); Hiroaki Aoyama, Kyoto (JP); Eisuke Yamazaki, Kyoto (JP); Minoru Taniguchi, Kyoto (JP); Chisato Tawara, Kyoto (JP); Shusuke Eshita, Kyoto (JP); Masayuki Fukutsuka, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 15/917,503

(22) Filed: Mar. 9, 2018

(65) Prior Publication Data
US 2018/0192946 A1    Jul. 12, 2018

Related U.S. Application Data

(63) Continuation of application No. PCT/JP2016/088932, filed on Dec. 27, 2016.

(30) Foreign Application Priority Data

Jan. 4, 2016 (JP) ................................. 2016-000257

(51) Int. Cl.
*A61B 5/022* (2006.01)
*A61B 5/00* (2006.01)
(Continued)

(52) U.S. Cl.
CPC .............. *A61B 5/681* (2013.01); *A61B 5/022* (2013.01); *A61B 5/7445* (2013.01);
(Continued)

(58) Field of Classification Search
CPC ....... A61B 5/022; A61B 5/681; G04G 21/025
See application file for complete search history.

(56) References Cited

U.S. PATENT DOCUMENTS 4,896,676 A * 1/1990 Sasaki ................ A61B 5/02241
600/494
5,033,471 A 7/1991 Yokoe et al.
(Continued)

FOREIGN PATENT DOCUMENTS

CN 201365917 Y 12/2009
CN 103300838 A 9/2013
(Continued)

OTHER PUBLICATIONS

International Search Report issued in Application No. PCT/JP2016/088932, dated Feb. 7, 2017 (1 page).
(Continued)

*Primary Examiner* — Puya Agahi
(74) *Attorney, Agent, or Firm* — Osha Liang LLP

(57) ABSTRACT

An appliance includes a belt that is worn by being wound around a wrist. The appliance includes: at least a first display region that is positioned in an area of the belt that corresponds to a volar-side surface or a radius-side surface of the wrist; and a second display region that is positioned in an area of the belt that corresponds to a back-side surface of the wrist. During a blood pressure measurement period, first control for displaying ongoing blood pressure measurement information only on the first display region is performed, and during a period other than the blood pressure measurement period, second control for displaying information that
(Continued)

needs to be displayed on the first or second display region is performed.

21 Claims, 22 Drawing Sheets

(51) Int. Cl.
| | |
|---|---|
| G04G 17/08 | (2006.01) |
| G04G 21/02 | (2010.01) |
| A61B 5/11 | (2006.01) |
| A61B 5/021 | (2006.01) |

(52) U.S. Cl.
CPC ......... *G04G 17/083* (2013.01); *G04G 21/025* (2013.01); *A61B 5/02108* (2013.01); *A61B 5/1116* (2013.01); *A61B 5/743* (2013.01)

(56) References Cited

U.S. PATENT DOCUMENTS

| | | | |
|---|---|---|---|
| 5,439,002 A | 8/1995 | Narimatsu et al. | |
| 5,778,879 A * | 7/1998 | Ota | A61B 5/022 600/310 |
| 6,216,490 B1 | 4/2001 | Radley-Smith | |
| 2003/0013976 A1* | 1/2003 | Freund | A61B 5/022 600/503 |
| 2007/0158376 A1 | 7/2007 | Radley-Smith | |
| 2007/0208258 A1* | 9/2007 | Whitaker | A61B 5/021 600/490 |
| 2009/0012409 A1* | 1/2009 | Roenneberg | A61B 5/022 600/485 |
| 2009/0156946 A1* | 6/2009 | Lane | A61B 5/022 600/490 |
| 2010/0286538 A1 | 11/2010 | Kim et al. | |
| 2011/0054329 A1* | 3/2011 | Katsumoto | A61B 5/021 600/490 |
| 2013/0222270 A1 | 8/2013 | Winkler et al. | |
| 2013/0222271 A1 | 8/2013 | Alberth et al. | |
| 2013/0245391 A1* | 9/2013 | Hyde | A61B 5/02208 600/301 |
| 2013/0271350 A1 | 10/2013 | Lyons | |
| 2014/0378794 A1 | 12/2014 | Conrad et al. | |
| 2015/0105676 A1 | 4/2015 | Uesaka et al. | |
| 2015/0182147 A1* | 7/2015 | Sato | A61B 5/02108 600/493 |
| 2015/0186092 A1* | 7/2015 | Francis | G06F 3/1423 345/520 |
| 2015/0213580 A1* | 7/2015 | Yamano | G09G 3/20 345/649 |
| 2015/0378312 A1* | 12/2015 | Modaragamage | A44C 5/24 368/10 |
| 2016/0267310 A1* | 9/2016 | AlNasser | G06K 7/10009 |
| 2017/0188668 A1* | 7/2017 | Watterson | A44C 5/0015 |
| 2017/0367649 A1 | 12/2017 | Kitagawa et al. | |

FOREIGN PATENT DOCUMENTS

| | | |
|---|---|---|
| CN | 105190479 A | 12/2015 |
| CN | 107205669 A | 9/2017 |
| JP | H01-209045 A | 8/1989 |
| JP | H01-242031 A | 9/1989 |
| JP | H02-261421 A | 10/1990 |
| JP | H04-099561 A | 3/1992 |
| JP | H06-11701 A | 1/1994 |
| JP | H6-102378 A | 4/1994 |
| JP | H07-124130 A | 5/1995 |
| JP | 2004-113368 A | 4/2004 |
| JP | 2004-254717 A | 9/2004 |
| JP | 2010-220948 A | 10/2010 |
| JP | 2010-220949 A | 10/2010 |
| WO | 01/064070 A1 | 9/2001 |
| WO | 2012/018029 A1 | 2/2012 |
| WO | 2013/157393 A1 | 10/2013 |
| WO | 2016/136866 A1 | 9/2016 |

OTHER PUBLICATIONS

Written Opinion issued in Application No. PCT/JP2016/088932, dated Feb. 7, 2017 (3 pages).
Decision to Grant a Patent issued in corresponding Japanese Application No. 2016-000257, dated May 23, 2017 (6 pages).
Office Action issued in Chinese Application No. 201680026400.7, dated Apr. 2, 2018 (16 pages).
International Search Report issued in Application No. PCT/JP2016/055588, dated May 24, 2016 (1 pages).
Written Opinion issued in International Application No. PCT/JP2016/055588, dated May 24, 2016 (4 pages).
Extended Search Report issued in European Application No. 16755610.9, dated Sep. 7, 2018 (9 pages).
Office Action issued in European Application No. 16755610.9, dated Apr. 24, 2019 (11 Pages).

* cited by examiner

APPLIANCE

TECHNICAL FIELD

The present invention relates to an appliance, and more specifically relates to an appliance having a plurality of functions including a blood pressure measurement function.

BACKGROUND ART

As this type of appliance, as disclosed in, for example, Patent Document 1 (JP H6-11701U), an appliance is conventionally known in which a blood pressure measurement apparatus is embedded in a digital wrist watch. The appliance includes one display device, and the time obtained by the digital watch and blood pressure values obtained by the blood pressure measurement apparatus are displayed on the display device by being selectively switched.

CITATION LIST

Patent Literature

Patent Document 1: JP H6-11701U
Patent Document 2: JP H6-102378A
Patent Document 3: U.S. Pat. No. 6,216,490

SUMMARY OF INVENTION

As with a commonly used wrist watch, the appliance disclosed in Patent Document 1 described above is usually worn, with the display device (and the main body in which the display device is embedded) being positioned on the back-side surface (dorsal-side surface) of a user's wrist. The reason is that if the above-described display device (and the main body in which the display device is embedded) is positioned on the volar-side surface (palm-side surface) of the wrist, this type of appliance that is worn constantly may disturb user's daily activities because the display device and the main body protrude from the volar-side surface of the wrist toward the user's trunk.

On the other hand, in the case where blood pressure measurement is performed by using a wrist-worn blood pressure measurement apparatus, the user is recommended to take a posture such that, for example, his/her arm is bent and the elbow is rested on a table, with the wrist being directed obliquely upward and forward and the volar-side surface (i.e., palm) of the wrist facing upward (this posture will be referred to as "recommended blood pressure measurement posture", see FIG. 6). The reason is to enhance the accuracy of blood pressure measurement. To be specific, this is to eliminate the height difference between a user's wrist 90 and the heart 91 as well as to cause the arteries (radial artery and ulnar artery) running through the wrist 90 to be positioned in situ along the outer surface (volar-side surface) of the wrist 90 and to prevent the arteries from being twisted around the bones (radius and ulna) of the wrist as much as possible.

Here, as described above, the appliance disclosed in Patent Document 1 is worn with the display device (and the main body) being positioned on the back-side surface of the user's wrist. For this reason, even if the user temporarily takes the recommended blood pressure measurement posture, a problem arises in that the user unconsciously twists the wrist so as to view the content displayed on the display device, and measurement is taken with the back-side surface facing upward. In this case, blood pressure measurement is taken with the arteries running through the wrist being twisted around the bones of the wrist, and thus the accuracy of blood pressure measurement is lowered.

Under the circumstances, one or more embodiments of the present invention provide an appliance that can prompt the user to take the recommended blood pressure measurement posture.

Accordingly, the appliance according to one or more embodiments of the present invention is an appliance having a plurality of functions including a blood pressure measurement function and including a belt that is worn by being wound around a wrist, the appliance including at least: a first display region that is positioned in an area of the belt that corresponds to a volar-side surface or a radius-side surface of the wrist; and a second display region that is positioned in an area of the belt that corresponds to a back-side surface of the wrist, wherein the appliance includes a control unit that performs first control for displaying ongoing blood pressure measurement information only on the first display region during a blood pressure measurement period and performs second control for displaying information that needs to be displayed on the first or second display region during a period other than the blood pressure measurement period.

In this specification, the term "volar-side surface" of the wrist refers to the surface of the palm-side portion of the outer circumference of the wrist. The term "radius-side surface" of the wrist refers to the surface of the thumb-side portion of the outer circumference of the wrist. The term "back-side surface" of the wrist refers to the surface of the dorsal-side portion of the outer circumference of the wrist.

Also, the term "blood pressure measurement period" refers to the period during which blood pressure measurement is taken, the period being from the start of blood pressure measurement to the completion of the blood pressure measurement. The term "the start of blood pressure measurement" encompasses a period during which a preparation for measurement is performed such as adjusting a pressure sensor to 0 mmHg.

Likewise, the term "ongoing blood pressure measurement information" refers to, for example, an indication of the progress of the blood pressure measurement, an indication of pressure and pulse waveforms of the wrist during the blood pressure measurement, an indication that the arm belt is loose, an indication that the body is moving, an indication of blood pressure values obtained through the blood pressure measurement, and the like. The term "ongoing blood pressure measurement information" also encompasses inquiry information for inquiring whether or not to start a blood pressure measurement period, posture guidance information for guiding a user to bring the posture of the wrist to which the appliance is attached to an appropriate posture, and worn wrist guidance information for guiding the user to detach the appliance from one of the wrists and attach the appliance to the other wrist. However, in order to display the inquiry information, the posture guidance information, and the worn wrist guidance information, exceptional control (third control, fourth control, and fifth control), which will be described later, is performed.

Also, the term "information that needs to be displayed" may include all information that needs to be displayed.

In a state in which the appliance according to one or more embodiments of the present invention is worn by being wound around a user's wrist, the first display region is positioned so as to correspond to the volar-side surface or the radius-side surface of the wrist. The second display region is positioned so as to correspond to the back-side surface of the wrist. In this state, the user who is trying to take blood pressure measurement takes a recommended blood pressure measurement posture in accordance with, for example, an instruction manual of the product, the recommended blood pressure measurement posture being typically a posture in which the user's arm is bent and the elbow is rested on a table, with the wrist being directed obliquely upward and forward and the volar-side surface of the wrist facing upward. Then, the control unit performs first control for displaying ongoing blood pressure measurement information only on the first display region (that is positioned so as to correspond to the volar-side surface or the radius-side surface of the wrist) during a blood pressure measurement period. As used herein, the recommended blood pressure measurement posture refers to a posture in which the first display region is facing the user's eyes. Accordingly, the user is prompted to view the ongoing blood pressure measurement information (for example, an indication of the progress of blood pressure measurement, or the like) displayed on the first display device while taking the recommended blood pressure measurement posture without performing an operation such as twisting the wrist. If blood pressure measurement is performed in this state, the accuracy of blood pressure measurement is enhanced. As described above, according to the appliance of one or more embodiments of the present invention, the user is prompted to take the recommended blood pressure measurement posture during a blood pressure measurement period.

In this specification, the term "recommended blood pressure measurement posture" typically refers to a posture in which, as described above, an arm is bent and the elbow is rested on a table, with the wrist being directed obliquely upward and forward and the volar-side surface of the wrist facing upward. However, the table is not a requirement. The term "recommended blood pressure measurement posture" may also refer to a posture in which an forearm is raised so as to intersect obliquely with respect to the trunk in front (the hand pointing upward and the elbow pointing downward), with the wrist being maintained at the heart height level and the radius-side surface of the wrist facing upward.

On the other hand, during a period other than the blood pressure measurement period, the control unit performs second control for displaying information that needs to be displayed (including ongoing blood pressure measurement information) on the first or second display region. Accordingly, the first and second display regions are used for a plurality of functions including the blood pressure measurement function.

Patent Document 2 (JP H6-102378), for example, discloses an appliance (information display apparatus) that is worn around a wrist and includes a plurality of display devices (display members) arranged in a circumferential direction of the appliance. Also, Patent Document 3 (U.S. Pat. No. 6,216,490) discloses an appliance (bracelet) that is worn around a wrist and includes a display element extending along the whole area of the appliance in a circumferential direction thereof. However, insofar as the applicant of the present application is aware, an appliance that is worn around a wrist and in which display regions are switched according to the blood pressure measurement function has not been achieved by a conventional technique.

With an appliance according to an embodiment, an operation unit for inputting an instruction to start the blood pressure measurement period is positioned in the area of the belt that corresponds to the volar-side surface or the radius-side surface of the wrist.

In a state in which the appliance according to the embodiment is worn around the user's wrist with the belt, the operation unit is positioned so as to correspond to the volar-side surface or the radius-side surface of the wrist. Accordingly, the user who is trying to take blood pressure measurement can easily input an instruction to start the blood pressure measurement period while taking the recommended blood pressure measurement posture and operating the operation unit with the other hand of the wrist to which the appliance is attached in accordance with, for example, the instruction manual of the product. With this configuration, in a state in which the user is taking the recommended blood pressure measurement posture, the blood pressure measurement period is started. Also, as described above, the user is prompted to take the recommended blood pressure measurement posture during the blood pressure measurement period. As a result, the accuracy of blood pressure measurement is enhanced.

In the appliance according to the embodiment, a starting unit that makes a transition to a start mode in which a preparation for starting the blood pressure measurement period is performed if a wrist posture of the wrist to which the appliance is attached is detected and the wrist posture matches a recommended blood pressure measurement posture, or if an instruction to perform the preparation for starting the blood pressure measurement period is input via the operation unit.

In this specification, the term "wrist posture" encompasses the inclination angle of the wrist (forearm) with respect to the horizontal surface (typically, table surface) and the angular position of the volar-side surface about the wrist.

Likewise, the expression "match the recommended blood pressure measurement posture" encompasses not only the case where the posture completely matches the recommended blood pressure measurement posture, but also the case where the posture is in a pre-set acceptable range of the recommended blood pressure measurement posture Also, the term "preparation for starting the blood pressure measurement period" encompasses, for example, settings with respect to the usage of the first and second display regions.

In the appliance according to the embodiment, the starting unit makes a transition to a start mode in which a preparation for starting the blood pressure measurement period is performed if a wrist posture of the wrist to which the appliance is attached is detected and the wrist posture matches a recommended blood pressure measurement posture, or if an instruction to perform the preparation for starting the blood pressure measurement period is input via the operation unit. With this configuration, the preparation for starting the blood pressure measurement period is performed while the user is taking the recommended blood pressure measurement posture or according to the user's request. Through the preparation for starting the blood pressure measurement period, the blood pressure measurement period is started smoothly.

With the appliance according to the embodiment, the starting unit makes a transition to the start mode if the wrist posture is brought within a pre-set first acceptable range of the recommended blood pressure measurement posture, and ends the start mode and starts the blood pressure measurement period if the wrist posture is brought within a pre-set second acceptable range during the start mode, the pre-set second acceptable range being a range that is set to be within the first acceptable range of the recommended blood pressure measurement posture.

As used herein, for example, the "first acceptable range" is set as a range enough to perform the preparation for starting the blood pressure measurement period. The "second acceptable range" is set as a range that is more preferable to start the blood pressure measurement period. The expression "the pre-set second acceptable range being a range that is set to be within the first acceptable range" typically means that the second acceptable range is smaller than the first acceptable range, but the second acceptable range may be set equal to the first acceptable range.

In the appliance according to the embodiment, the starting unit makes a transition to the start mode if the wrist posture is brought within a pre-set first acceptable range of the recommended blood pressure measurement posture. Accordingly, the preparation for starting the blood pressure measurement period is performed while the user is substantially taking the recommended blood pressure measurement posture. Also, during the start mode, if the wrist posture is brought within a pre-set second acceptable range that is set to be within the first acceptable range of the recommended blood pressure measurement posture, the start mode is ended, and the blood pressure measurement period is started. Accordingly, in a state in which the user is taking a posture closer to the recommended blood pressure measurement posture, the blood pressure measurement period is started.

With the appliance according to the embodiment, during the start mode, the control unit performs third control for displaying inquiry information for inquiring whether or not to start the blood pressure measurement period only on the first display region.

In the appliance according to the embodiment, during the start mode, the control unit performs third control for displaying inquiry information for inquiring whether or not to start the blood pressure measurement period only on the first display region. Accordingly, upon looking at the inquiry information displayed on the first display region, the user is prompted to make a decision as to whether or not to perform blood pressure measurement, or in other words, whether or not to start the blood pressure measurement period. If the user makes a decision to start the blood pressure measurement period, the user can input an instruction to start the blood pressure measurement period through the operation unit. With this configuration, the blood pressure measurement period can be started according to the user's request.

With the appliance according to the embodiment, the control unit ends the start mode and starts the blood pressure measurement period if an instruction to start the blood pressure measurement period is input via the operation unit after the control unit has displayed the inquiry information on the first display region.

In the appliance according to the embodiment, the blood pressure measurement period can be started according to the user's request after the inquiry information has been displayed on the first display region.

With the appliance according to the embodiment, the control unit performs fourth control for displaying posture guidance information for guiding a user to bring a wrist posture of the wrist to which the appliance is attached so as to match a recommended blood pressure measurement posture on the first or second display region even during the blood pressure measurement period.

If the wrist posture of the wrist to which the appliance is attached does not match the recommended blood pressure measurement posture, for example, if the volar-side surface of the wrist is facing downward, the first display region is invisible from the user, and only the second display region is visible from the user. In this case, it is necessary to prompt the user to bring the wrist posture to match the recommended blood pressure measurement posture, but simply displaying the posture guidance information for prompting the user to bring the wrist posture to match the recommended blood pressure measurement posture only on the first display region according to the first control is not effective in prompting the user to bring the wrist posture to match the recommended blood pressure measurement posture because the first display region is invisible from the user. To address this, in the appliance according to the embodiment, the control unit performs fourth control for displaying posture guidance information for guiding the user to bring the wrist posture of the wrist to which the appliance is attached so as to match the recommended blood pressure measurement posture on the first or second display region even during the blood pressure measurement period. That is, the "posture guidance information" is displayed not only on the first display region but also exceptionally on the second display region even during the blood pressure measurement period. During a period other than the blood pressure measurement period, the "posture guidance information" is displayed on the first or second display region according to the second control. Accordingly, looking at the posture guidance information displayed on the first or second display region, the user is prompted to bring the wrist posture to match the recommended blood pressure measurement posture. As a result of the guidance, blood pressures are measured while the user is taking the recommended blood pressure measurement posture, and thus the accuracy of blood pressure measurement is enhanced.

With the appliance according to the embodiment, if it is determined, as a result of detection as to which of a left wrist and a right wrist the appliance is attached to, that the appliance is attached to one of the wrists, the control unit performs fifth control for displaying worn wrist guidance information for guiding a user to detach the appliance from the wrist and then attach the appliance to the other wrist on the first or second display region even during the blood pressure measurement period.

For example, the term "one of the wrists" refers to one of the left wrist and the right wrist to which the appliance is not intended to be attached. The term "the other wrist" refers to one of the left wrist and the right wrist to which the appliance is intended to be attached.

In the appliance according to the embodiment, the control unit detects which of the left wrist and the right wrist the appliance is attached to. Then, if the appliance is attached to one of the wrists (for example, the right wrist), worn wrist guidance information for guiding the user to detach the appliance from the wrist and then attach the appliance to the other wrist (for example, the left wrist) is displayed on the first or second display region even during the blood pressure measurement period. That is, the "worn wrist guidance information" is displayed not only on the first display region but also exceptionally on the second display region even during the blood pressure measurement period. During a period other than the blood pressure measurement period, the "worn wrist guidance information" is displayed on the first or second display region according to the second control. Accordingly, looking at the worn wrist guidance information displayed on the first or second display region, the user is prompted to detach the appliance from one of the wrists and then attach the appliance to the other wrist. As a result of the guidance, blood pressures are measured in the other wrist (for example, the left wrist), and thus the accuracy of blood pressure measurement is enhanced.

With the appliance according to the embodiment, the control unit displays the posture guidance information on the first or second display region by using an image including a hand or a wrist, or by illuminating or blinking light.

In this specification, "image including a hand or a wrist" may be a still image such as an illustration or a picture, or may be a moving image such as an animation or a video clip. The "image including a hand or a wrist" may include a hand and a wrist, or may include the upper part of the body.

In the appliance according to the embodiment, the control unit displays the posture guidance information on the first or second display region by using an image including a hand or a wrist, or by illuminating or blinking light. Accordingly, the user can intuitively understand the content of the posture guidance information by looking at the image or the light.

With the appliance according to the embodiment, the control unit displays the worn wrist guidance information on the first or second display region by using an image including a hand or a wrist, or by illuminating or blinking light.

In the appliance according to the embodiment, the control unit displays the worn wrist guidance information on the first or second display region by using an image including a hand or a wrist, or by illuminating or blinking light. Accordingly, the user can intuitively understand the content of the worn wrist guidance information by looking at the image or the light.

The appliance according to the embodiment includes a sound emitting unit that emits a sound or a vibrator that vibrates, and the control unit informs a user of posture guidance information for guiding the user to bring a wrist posture of the wrist to which the appliance is attached so as to match a recommended blood pressure measurement posture by using the sound from the sound emitting unit or the vibration of the vibrator.

In the appliance according to the embodiment, the control unit informs a user of posture guidance information for guiding the user to bring a wrist posture of the wrist to which the appliance is attached so as to match a recommended blood pressure measurement posture by using the sound from the sound emitting unit or the vibration of the vibrator. Accordingly, with the sound or the vibration, the user is prompted to bring the wrist posture to match the recommended blood pressure measurement posture.

The appliance according to the embodiment includes a sound emitting unit that emits a sound or a vibrator that vibrates, and if it is determined, as a result of detection as to which of a left wrist and a right wrist the appliance is attached to, that the appliance is attached to one of the wrists, the control unit informs a user of worn wrist guidance information for guiding the user to detach the appliance from the one of the wrists and then attach the appliance to the other wrist by using the sound from the sound emitting unit or the vibration of the vibrator.

In the appliance according to the embodiment, if it is determined, as a result of detection as to which of a left wrist and a right wrist the appliance is attached to, that the appliance is attached to one of the wrists, the control unit informs a user of worn wrist guidance information for guiding the user to detach the appliance from the one of the wrists and then attach the appliance to the other wrist by using the sound from the sound emitting unit or the vibration of the vibrator. Accordingly, with the sound or the vibration, the user is prompted to detach the appliance from one of the wrists and attach the appliance to the other wrist.

The appliance according to the embodiment includes: a first operation unit for inputting an instruction to perform a function of the appliance, the first operation unit being positioned in the area of the belt that corresponds to the volar-side surface or the radius-side surface of the wrist; and a second operation unit for inputting an instruction to perform a function of the appliance, the second operation unit being positioned in the area of the belt that corresponds to the back-side surface of the wrist, and an instruction to start the blood pressure measurement period can be input only via the first operation unit among the first and second operation units.

As used herein, the expression "can be input only via the first operation unit among the first and second operation units" means that the instruction to start the blood pressure measurement period can be input only via the first operation unit, and cannot be input via the second operation unit. This does not exclude the case where the input of the instruction to start the blood pressure measurement period is performed by using any other means other than the first and second operation units. For example, the case where the preparation for starting the blood pressure measurement period is performed (or started) if it is determined, as a result of detecting the wrist posture by the acceleration sensor, that the wrist posture matches the recommended blood pressure measurement posture is not excluded.

In a state in which the appliance according to the embodiment is worn around the user's wrist, the first operation unit is positioned so as to correspond to the volar-side surface or the radius-side surface of the wrist. The second operation unit is positioned in the area of the belt that corresponds to the back-side surface of the wrist. The user can input an instruction to perform any function of the appliance by operating the first operation unit or the second operation unit with the other hand of the wrist to which the appliance is attached. Here, in the appliance according to the embodiment, the instruction to start the blood pressure measurement period can be input only via the first operation unit among the first and second operation units. The first operation unit is positioned so as to correspond to the volar-side surface or the radius-side surface of the wrist, and thus the user who is trying to take blood pressure measurement is prompted to unconsciously take the recommended blood pressure measurement posture so as to try to operate the first operation unit with the other hand of the wrist to which the appliance is attached, and operate the first operation unit while taking the recommended blood pressure measurement posture. Also, as described above, during the blood pressure measurement period, the ongoing blood pressure measurement information is displayed only on the first display region (that is positioned so as to correspond to the volar-side surface or the radius-side surface of the wrist), and thus the user is prompted to take the recommended blood pressure measurement posture. As a result, the accuracy of blood pressure measurement is enhanced.

An appliance according to one or more embodiments of the present invention is an appliance having a plurality of functions including a blood pressure measurement function and including a belt that is worn by being wound around a wrist, the appliance including: a first operation unit for inputting an instruction to perform a function of the appliance, the first operation unit being positioned in an area of the belt that corresponds to a volar-side surface or a radius-side surface of the wrist; and a second operation unit for inputting an instruction to perform a function of the appliance, the second operation unit being positioned in an area of the belt that corresponds to a back-side surface of the wrist, wherein an instruction to start a blood pressure measurement period can be input only via the first operation unit among the first and second operation units.

In a state in which the appliance according to the embodiment is worn around the user's wrist, the first operation unit is positioned so as to correspond to the volar-side surface or the radius-side surface of the wrist. The second operation unit is positioned in the area of the belt that corresponds to the back-side surface of the wrist. The user can input an instruction to perform any function of the appliance by operating the first operation unit or the second operation unit with the other hand of the wrist to which the appliance is attached. Here, in the appliance according to the embodiment, the instruction to start the blood pressure measurement period can be input only via the first operation unit among the first and second operation units. The first operation unit is positioned so as to correspond to the volar-side surface or the radius-side surface of the wrist, and thus the user who is trying to take blood pressure measurement is prompted to unconsciously take the recommended blood pressure measurement posture so as to try to operate the first operation unit with the other hand of the wrist to which the appliance is attached, and operate the first operation unit while taking the recommended blood pressure measurement posture. Also, the user can easily and continuously take the recommended blood pressure measurement posture during the blood pressure measurement period. As a result, the accuracy of blood pressure measurement is enhanced.

Advantageous Effects of the Invention

As is evident from the above description, with the appliance according to one or more embodiments of the present invention, it is possible to prompt the user to take the recommended blood pressure measurement posture.

DESCRIPTION OF EMBODIMENTS

Hereinafter, one or more embodiments of the present invention will be described in detail with reference to the drawings.

(Configuration of Appliance)

Figure 1A:
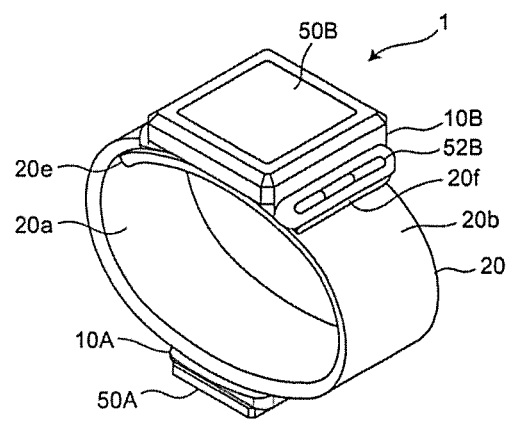
FIG. 1(A) is a perspective view of an external appearance of an appliance according to an embodiment of the present invention.
Figure 1B:
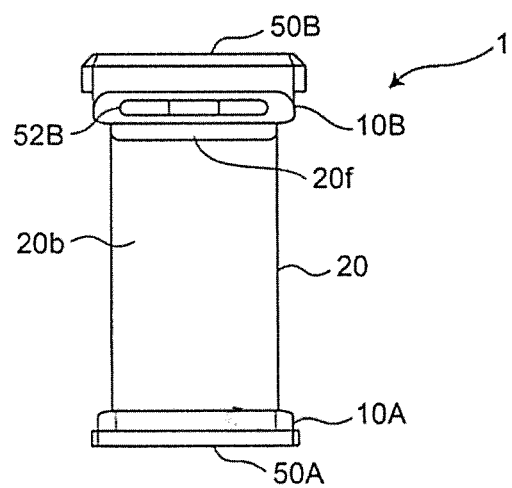
FIG. 1(B) is a right side view of the appliance shown in FIG. 1(A).
Figure 1C:
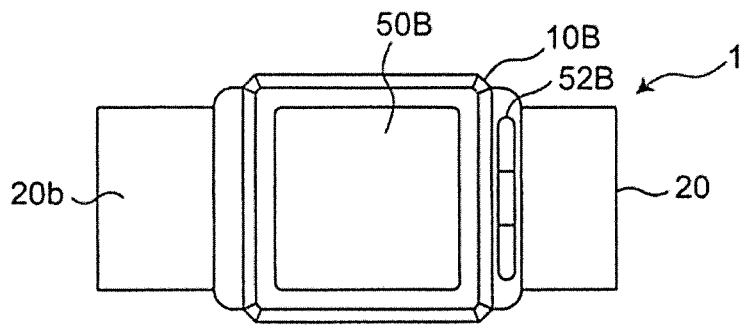
FIG. 1(C) is a top view of the appliance shown in FIG. 1(A).
Figure 1D:
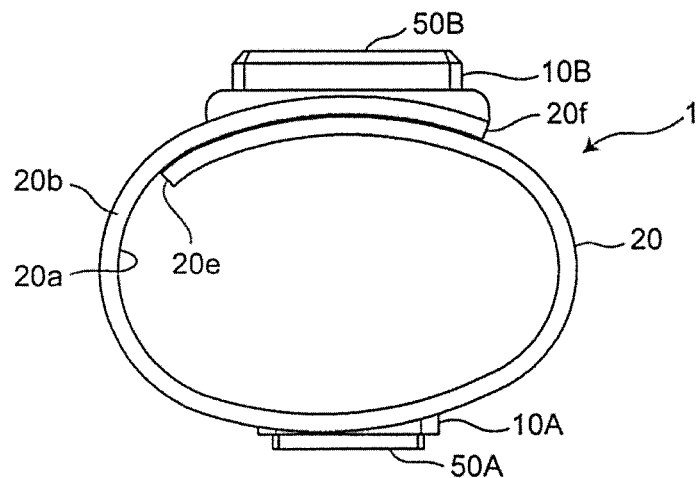
FIG. 1(D) is a front view of the appliance shown in FIG. 1(A).
Figure 1E:
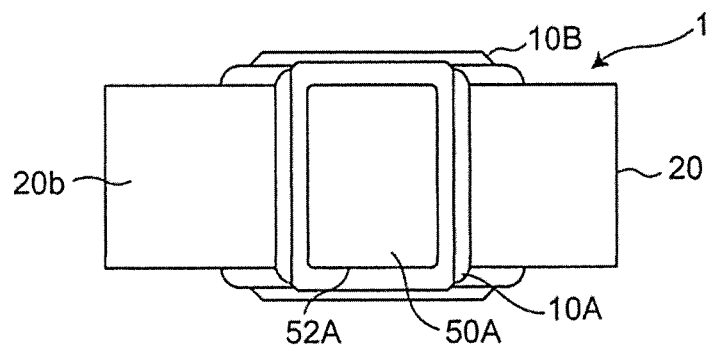
FIG. 1(E) is a bottom view of the appliance shown in FIG. 1(A).
Figure 2:
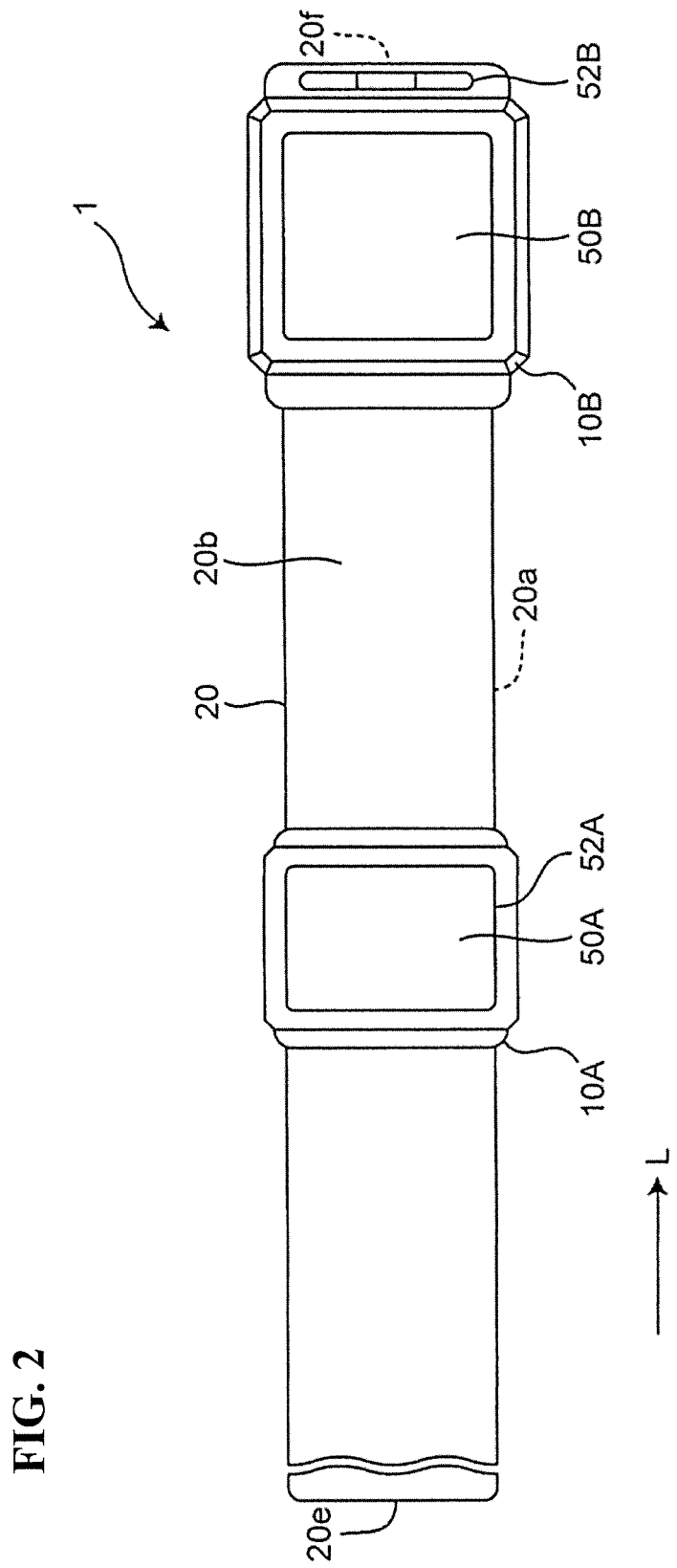
FIG. 2 is a plan view of the appliance in a laid-out state.

FIG. 1(A) shows an external appearance of an appliance (the entirety is indicated by reference numeral 1) according to an embodiment of the present invention as viewed obliquely, the appliance having a plurality of functions including a blood pressure measurement function. FIGS. 1(B), 1(C), 1(D), and 1(E) are a right side view, a top view, a front view, and a bottom view of the appliance 1 shown in FIG. 1(A), respectively. FIG. 2 shows the appliance 1 in a laid-out state. The appliance 1 is designed to be worn around the left wrist of the user.

As shown in the diagrams, the appliance 1 roughly includes a belt 20 that is to be wound around the left wrist of the user and two main bodies 10A and 10B that are attached unitarily to the belt 20.

The belt 20 has an elongated shape so as to be wound around the left wrist along the circumferential direction, and includes a strip-shaped inner layer 20a that is to be brought into contact with the left wrist and an outer layer 20b opposing the inner layer 20a. In this example, the inner layer 20a and the outer layer 20b are formed into a bladder by their peripheral edges being fused. The belt 20 is internally provided with a fluid bladder 21 for compressing the left wrist (see FIG. 3).

The inner layer 20a has a surface (an inner circumferential surface that is to be brought into contact with the left wrist) on which a large number of fine hooks (not shown) are provided so as to constitute a hook-and-loop fastener. On the other hand, the outer layer 20b has a surface (an outer circumferential surface) on which a large number of fine loops (not shown) that engage with the hooks are provided.

The main bodies 10A and 10B each have a substantially rectangular parallelepipedal outer shape. In this example, the main body 10B is configured to be thicker and larger than the main body 10A due to the number of mounted components described later. The main body 10A is configured to be thinner and smaller than the main body 10B so as to not disturb user's daily activities.

The main body 10A is attached unitarily to a substantially central area between one end (the end that is brought to an inner side when worn) 20e and another end (the end that is brought to an outer side when worn) 20f of the belt 20 in a circumferential direction (corresponding to a lengthwise direction L in FIG. 2) of the belt 20. A touch sensitive first display device 50A that serves as a first display region is provided on an outer surface of the main body 10A. Also, a first operation unit 52A is provided on the main body 10A as an operation unit for inputting an instruction to perform a function of the appliance.

The main body 10B is attached unitarily to an area of the belt 20 in the circumferential direction (corresponding to the lengthwise direction L in FIG. 2), the area being near the end 20f that is brought to an outer side when worn. A touch sensitive second display device 50B that serves as a second display region is provided on an outer surface of the main body 10B. Also, a second operation unit 52B for inputting an instruction to perform a function of the appliance is provided on the main body 10B.

Figure 5A:
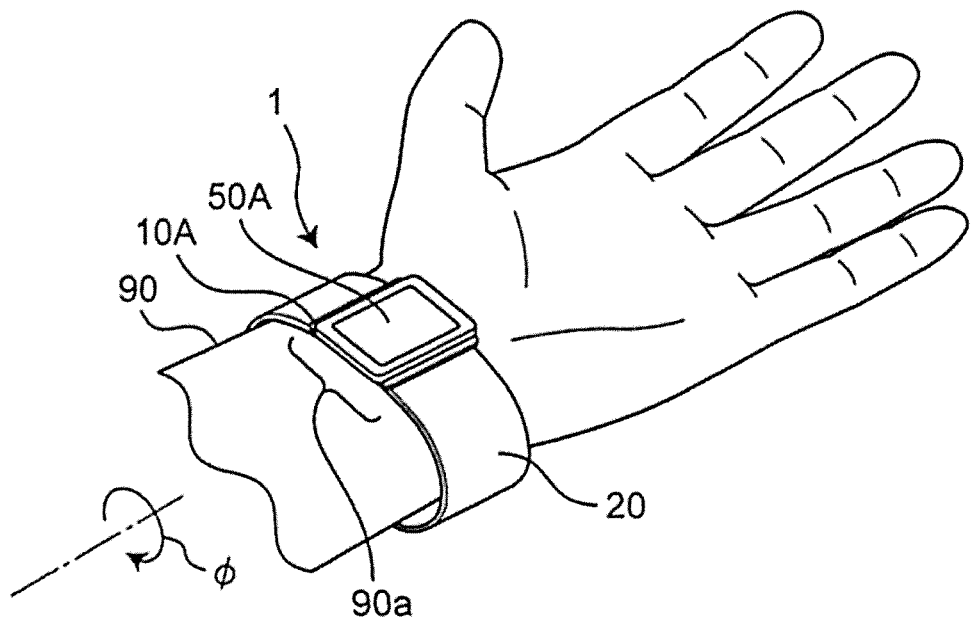
FIG. 5(A) is a diagram showing the appliance being worn around the user's left wrist (volar-side surface).
Figure 5B:
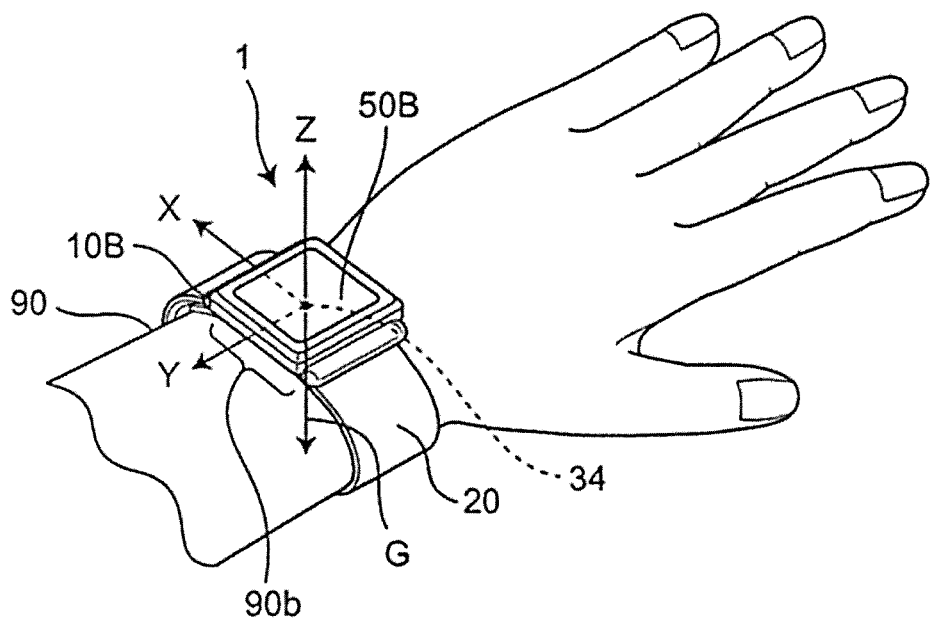
FIG. 5(B) is a diagram showing the appliance being worn around the user's left wrist (back-side surface).

In this example, as shown in FIG. 5(A) and FIG. 5(B), in order to attach the appliance 1 to a left wrist 90, the belt 20 is wound around the left wrist 90. A surface of the inner layer 20a that is near the end 20f of the belt 20 is pressed against a corresponding surface of the outer layer 20b and fixed by the above-described hook-and-loop fastener. At this time, as shown in FIG. 5(A), the first display device 50A (and the main body 10A) is positioned so as to correspond to a volar-side surface (the surface of the palm-side portion of the outer circumference of the wrist) 90a of the left wrist 90, and as shown in FIG. 5(B), the second display device 50B (and the main body 10B) is positioned so as to correspond to a back-side surface (the surface of the dorsal-side portion of the outer circumference of the wrist) 90b of the left wrist 90.

Figure 3:
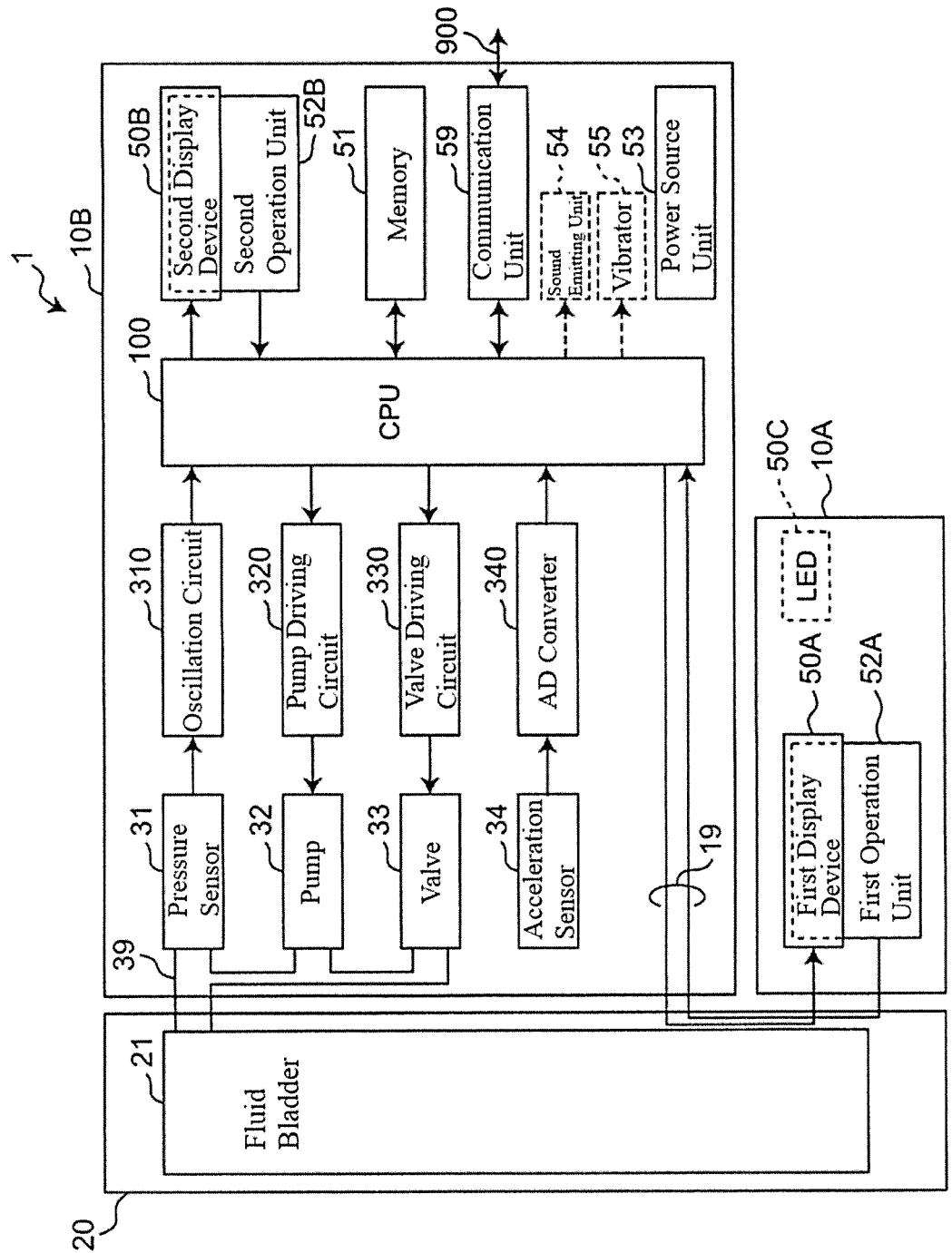
FIG. 3 is a diagram showing a block configuration of the appliance.

FIG. 3 shows a schematic block configuration of the belt 20 and the main bodies 10A and 10B of the appliance 1. The appliance 1 has, in addition to the blood pressure measurement function, a plurality of functions such as a clock function, a body temperature measurement function, and an activity amount measurement function.

The main body 10A of the appliance 1 incorporates the first display device 50A and the first operation unit 52A that were mentioned above. The main body 10B incorporates a CPU (Central Processing Unit) 100 that serves as a control unit, the second display device 50B, the second operation unit 52B, a memory 51 that serves as a storage unit, a communication unit 59, a power source unit 53, a pump 32, a valve 33, a pressure sensor 31, and an acceleration sensor 34. Furthermore, the main body 10B incorporates an oscillation circuit 310 that converts an output from the pressure sensor 31 to a frequency, a pump driving circuit 320 that drives the pump 32, a valve driving circuit 330 that drives the valve 33, and an AD converter 340 that performs AD (Analog to Digital) conversion on an output from the acceleration sensor 34. In this example, the first display device 50A and the first operation unit 52A incorporated in the main body 10A are electrically connected to the CPU 100 in the main body 10B via wiring 19 extending through the belt 20.

In this example, the display devices 50A and 50B are organic EL (Electro Luminescence) displays, and display various types of information in accordance with control signals from the CPU 100. Examples of information that needs to be displayed include blood pressure values obtained through blood pressure measurement, other information regarding blood pressure, the time obtained by the clock function, a value of body temperature measured by the body temperature measurement function, and a value of activity amount measured by the activity amount measurement function. On which of the display devices 50A and 50B such information is to be displayed, and when (how long) such information is to be displayed will be described later. The type of the display devices 50A and 50B is not limited to an organic EL display, and it is possible to use other types of display device such as an LCD (Liquid Cristal Display).

The first operation unit 52A includes a push switch. The push switch includes a stroke member (constituted by the display device 50A) that is supported by an elastic member (not shown) so as to be capable of moving up and down with respect to the main body 10A, and a contact (not shown) that is provided inside the main body 10A and is turned on or off depending on whether the stroke member moves up or down. In this example, in response to the push switch being pressed by the user, as an instruction for implementing a function of the appliance 1, for example, an operation signal for starting blood pressure measurement (a blood pressure measurement period) is input into the CPU 100.

The second operation unit 52B includes a plurality of (three in this example) push switches that are provided on a frame member that constitutes the main body 10B. In response to these push switches being pressed by the user, as instructions for implementing functions of the appliance 1, various operation signals are input into the CPU 100. Note, however, that the appliance 1 is configured such that an operation signal for starting blood pressure measurement (a blood pressure measurement period) can be input only via the first operation unit 52A, and cannot be input via the second operation unit 52B.

Also, in this example, the operation units 52A and 52B include touch panels provided on the outer surfaces of the display devices 50A and 50B, respectively. The touch panels may be pressure sensitive (resistive) touch panels or proximity (electrostatic capacitance) touch panels. The operation signals are also input into the CPU 100 via the touch panels in response to the user pressing a soft keypad (not shown) displayed on the display devices 50A and 50B in accordance with a control signal from the CPU 100. If, for example, the user presses a "start blood pressure measurement" switch (not shown) displayed on the first display device 50A, an instruction to start blood pressure measurement may be input. It is also possible to provide a microphone (not shown) so as to input an instruction to start blood pressure measurement by using the voice of the user.

The memory 51 stores, in a non-transitory manner, data of a program for controlling the appliance 1, data used to control the appliance 1, settings data for setting various types of functions of the appliance 1, data regarding measured blood pressure values, and the like. Also, the memory 51 is used as a work memory when a program is executed.

The CPU 100 serves as a control unit and executes various types of functions in accordance with the program for controlling the appliance 1 stored in the memory 51. For example, in the case of executing the blood pressure measurement function, the CPU 100 performs control for driving the pump 32 and the valve 33 in accordance with an operation signal from the first operation unit 52A. Also, the CPU 100 performs control for calculating blood pressure values based on a signal from the pressure sensor 31. Furthermore, the CPU 100 performs control for detecting the posture of the user based on an output from the acceleration sensor 34.

The communication unit 59 performs operation under control of the CPU 100 such as transmitting predetermined information to an external apparatus via a network 900 and receiving information from an external apparatus via the network 900 and transferring the received information to the CPU 100. The communication via the network 900 may be performed in a wireless or wired manner. In the present embodiment, the Internet is used as the network 900, but the network 900 is not limited thereto, and may be other types of networks such as an intra-hospital LAN (Local Area Network). Alternatively, it is possible to perform one-to-one communication by using a USB cable or the like.

The power source unit 53 supplies power to each of the CPU 100, the pressure sensor 31, the pump 32, the valve 33, the acceleration sensor 34, the display devices 50A and 50B, the operation units 52A and 52B, the memory 51, the communication unit 59, the oscillation circuit 310, the pump driving circuit 320, the valve driving circuit 330, and the AD converter 340.

The pump 32, the valve 33, and the pressure sensor 31 are connected to the fluid bladder 21 that is internally provided in the belt 20 via a common air conduit 39 that serves as a conduit system. The pump 32 supplies air to the fluid bladder 21 via the air conduit 39 in order to increase the pressure (cuff pressure) in the fluid bladder 21 that is internally provided in the belt 20. The valve 33 is a solenoid valve that is controlled to be opened or closed by turning on or off electricity, and is used to control the cuff pressure by discharging or trapping the air in the fluid bladder 21 through the air conduit 39. The pump driving circuit 320 drives the pump 32 based on a control signal provided from the CPU 100. The valve driving circuit 330 opens and closes the valve 33 based on a control signal provided from the CPU 100.

The pressure sensor 31 is, in this example, a piezoresistive pressure sensor, and detects the pressure in the belt 20 (the fluid bladder 21), in this example, a pressure based on the atmospheric pressure (being set to zero), via the air conduit 39 and outputs the detected pressure as a time-series cuff pressure signal Pc. The oscillation circuit 310 performs oscillation based on an electric signal value based on a change in electric resistance due to piezoresistance effect from the pressure sensor 31, and outputs a frequency signal having a frequency corresponding to the electric signal value of the pressure sensor 31 to the CPU 100.

In this example, the output from the pressure sensor 31 is used to calculate user's blood pressure values (including a systolic blood pressure and a diastolic blood pressure, the same applies hereinafter) by an oscillometric method. The output from the pressure sensor 31 is also used to calculate the pulse.

The acceleration sensor 34 is a three-axis acceleration sensor incorporated unitarily in the main body 10B. The acceleration sensor 34 outputs an acceleration signal to the CPU 100 via the AD converter 340 as a digital signal, the acceleration signal representing an acceleration in three mutually perpendicular directions of the belt 20 of the main body 10B, to be specific, the belt 20 attached unitarily to the main body 10B.

In this example, as shown in FIG. 5(B), an XYZ orthogonal coordinate system is set with the position of the acceleration sensor 34 in the main body 10B being taken as the origin. In this example, the Z axis is set so as to extend vertically with respect to the outer surface of the main body 10B toward the outside. The Y axis is set so as to extend in a direction from the hand toward the elbow along the left wrist 90 of the user, with the appliance 1 being worn around the left wrist 90 as already described. Likewise, the X axis is set so as to extend perpendicularly to the Y axis and the Z axis (extend substantially toward the left as viewed from the user in FIG. 5(B)).

In this example, the output from the acceleration sensor 34 is used to detect the posture of the left wrist 90 of the user (whether or not the user is taking a posture in which the wrist is being directed obliquely upward and forward and the palm is facing upward) according to the direction of gravitational acceleration vector G with respect to the XYZ orthogonal coordinate system. The method for detecting the wrist posture by using the output from the acceleration sensor 34 is known from, for example, JP 2007-054648A, JP 2014-064666A and the like, and thus a detailed description thereof is omitted in this specification.

Also, the output from the acceleration sensor 34 is used to detect which of the left wrist and the right wrist the appliance 1 is attached to according to the direction of gravitational acceleration vector G with respect to the XYZ orthogonal coordinate system. The method for detecting which of the left wrist and the right wrist the appliance 1 is attached to is known from, for example, JP 2008-307207A and the like, and thus a detailed description thereof is omitted in this specification.

In the appliance 1, the clock function is implemented by a clock incorporated in the CPU 100. The body temperature measurement function is implemented by using an output from a thermometer (not shown). The activity amount measurement function is implemented by using the output from the acceleration sensor 34.

(Blood Pressure Measurement Function and Display Example)

Figure 6:
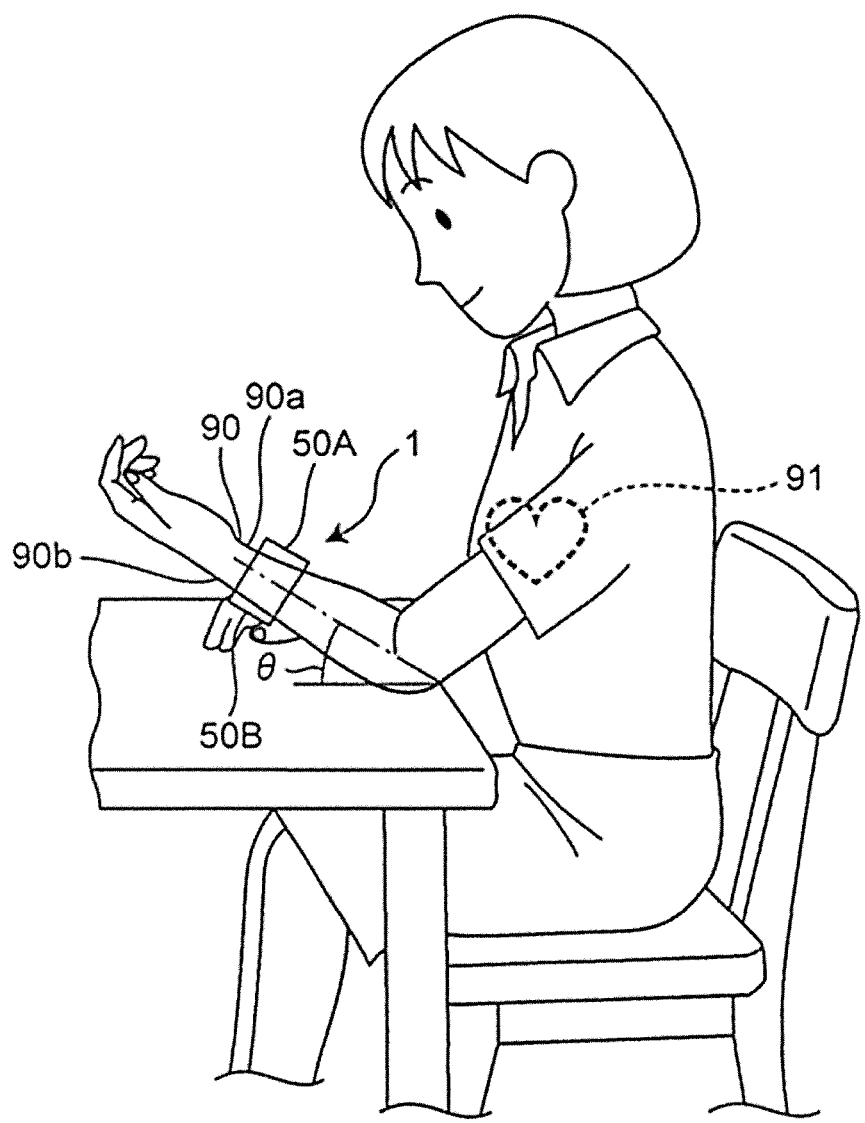
FIG. 6 is a diagram showing a user who is wearing the appliance around the left wrist and taking a recommended blood pressure measurement posture.
Figure 8A:
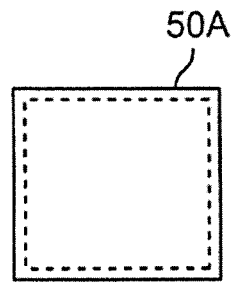
FIGS. 8(A) and 8(B) are diagrams showing display examples of a first display device and a second display device, respectively, at the time when the user takes a posture for blood pressure measurement.
Figure 8B:
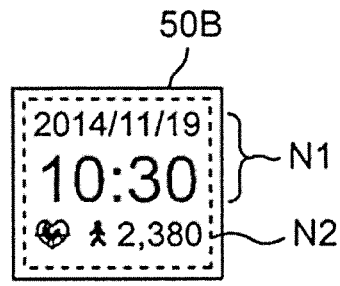

As shown in FIGS. 5(A) and 5(B), in a state in which the appliance 1 is worn around the left wrist 90 of the user, the display devices 50A and 50B are positioned so as to correspond to a volar-side surface 90a and a back-side surface 90b of the left wrist 90, respectively. In this state, the user takes a recommended blood pressure measurement posture as shown in FIG. 6 in accordance with, for example, the instruction manual of the product so as to perform blood pressure measurement, the recommended blood pressure measurement posture being a posture in which the user's arm is bent and the elbow is rested on a table, with the left wrist 90 being directed obliquely upward and forward and the volar-side surface of the left wrist 90 facing upward. It is assumed here that at this point in time, as shown in FIG. 8(A), the first display device 50A is in a non-display mode, and as shown in FIG. 8(B), the second display device 50B is in a display mode that shows an indication N1 (including an indication of the date "2014/11/19" and an indication of the time "10:30" in this example) generated by the clock function and an indication N2 (an indication of the step count "2,380" in this example) generated by the activity amount measurement function.

Figure 7:
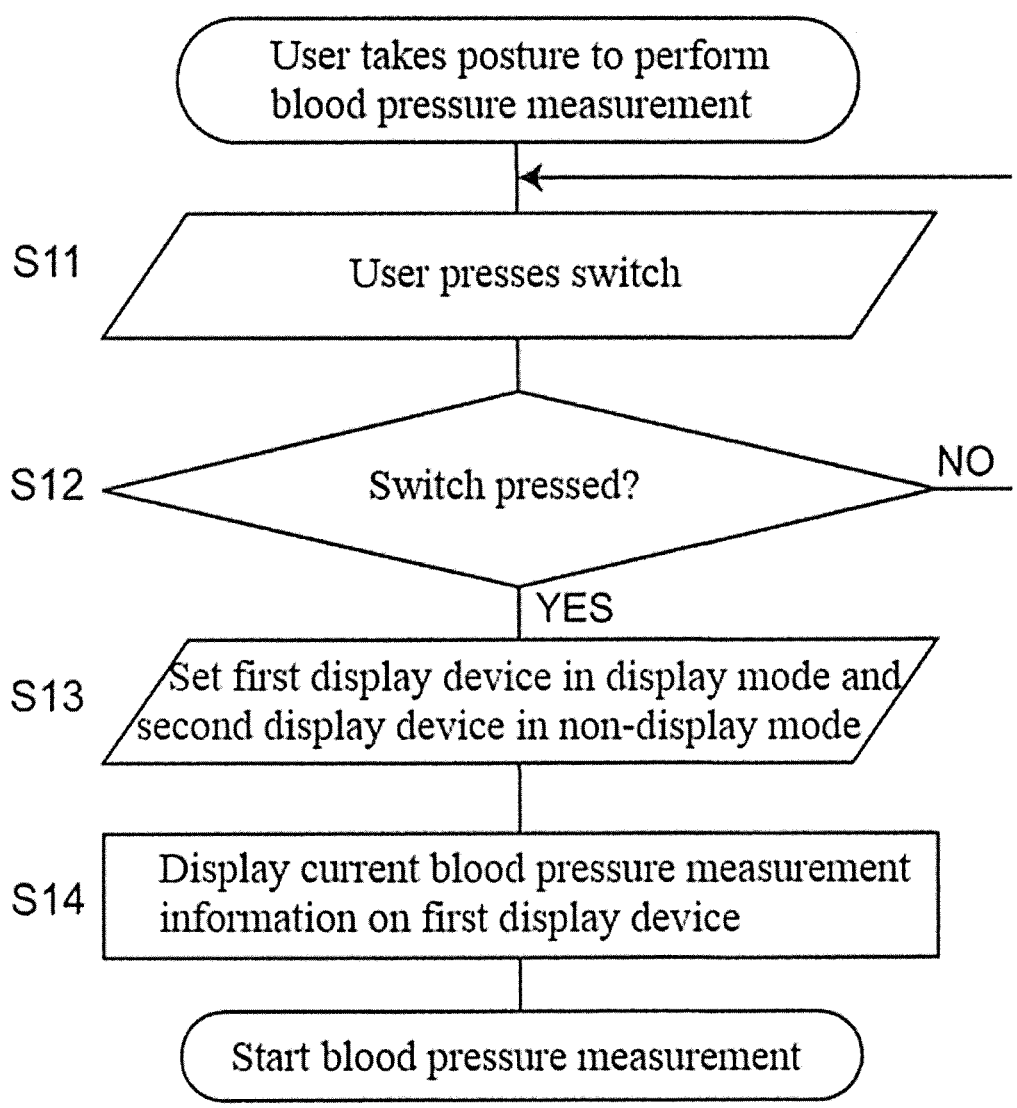
FIG. 7 is a diagram showing an example of an operational flowchart of display processing performed during a period from when the user takes a posture for blood pressure measurement until the start of blood pressure measurement.

In this state, as shown in step S11 of FIG. 7, if, for example, the user presses a push switch that servers as the first operation unit 52A provided in the main body 10A with the right hand (YES in step S12 in FIG. 7), the CPU 100 determines that an instruction to start blood pressure measurement (a blood pressure measurement period) has been input. In this way, the user can easily input an instruction to start a blood pressure measurement period by operating the first operation unit 52A with the other hand (the right hand in this example) of the left wrist 90 while taking the recommended blood pressure measurement posture.

Here, a situation may arise in which the user does not pay attention to take the recommended blood pressure measurement posture. However, in a state in which the appliance 1 is worn around the left wrist 90 of the user, the first operation unit 52A is positioned on the volar-side surface 90a of the left wrist 90. Accordingly, even in such a situation, the user who is trying to take blood pressure measurement is prompted to unconsciously take the recommended blood pressure measurement posture so as to try to operate the first operation unit 52A with the right hand, and operate the first operation unit 52A while taking the recommended blood pressure measurement posture. Also, the user can easily and continuously take the recommended blood pressure measurement posture during a blood pressure measurement period, which will be described next.

Figure 9A:
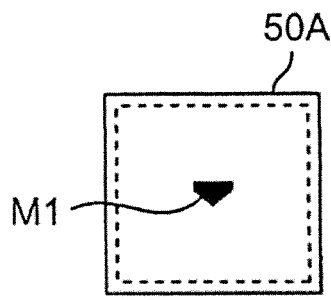
FIGS. 9(A) and 9(B) are diagrams showing display examples of the first display device and the second display device, respectively, at the start of blood pressure measurement.
Figure 9B:
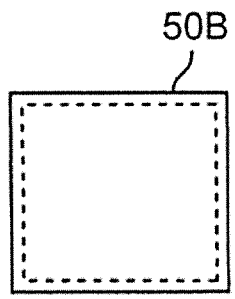

Next, the CPU 100 sets the first display device 50A in a display mode and the second display device 50B in a non-display mode (step S13 in FIG. 7), and then displays (currently) ongoing blood pressure measurement information A on the first display device 50A (step S14 in FIG. 7). In this example, as shown in FIG. 9(A), as the current blood pressure measurement information, a drop down arrow mark M1 that indicates that blood pressure measurement is under preparation is displayed on the first display device 50A. On the other hand, as shown in FIG. 9(B), the second display device 50B goes blank. In this way, the CPU 100 displays the current blood pressure measurement information only on the first display device 50A (first control). The blood pressure measurement (a blood pressure measurement period) is then started.

Figure 4:
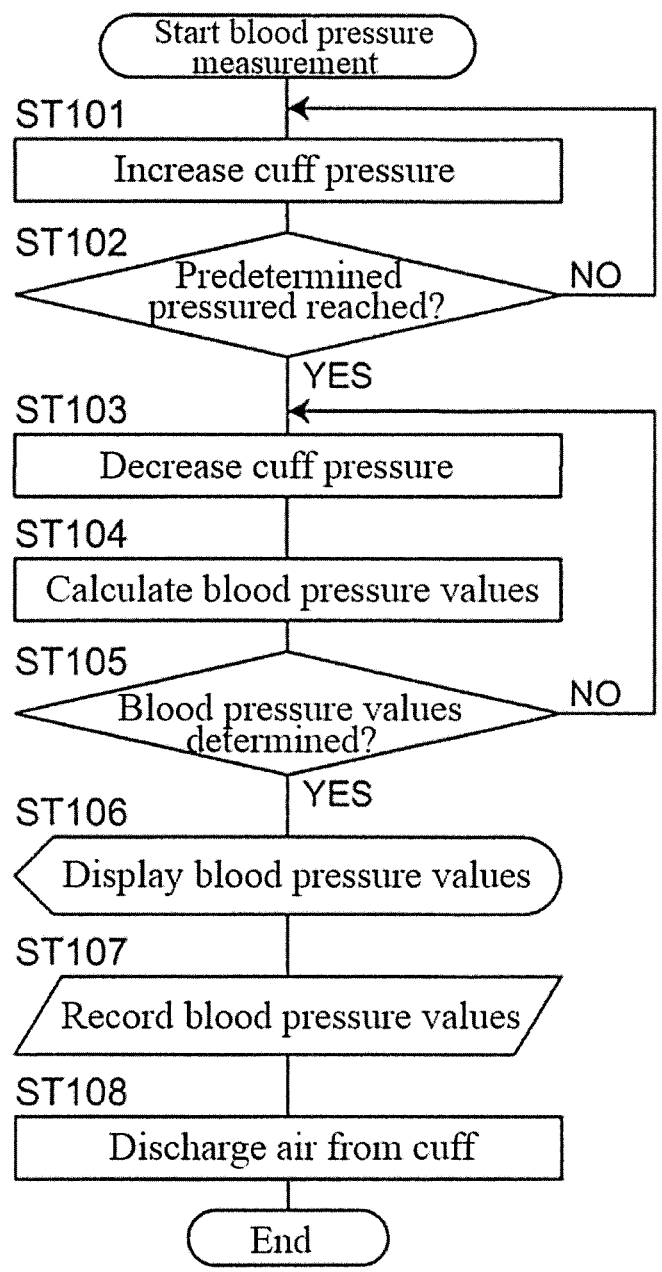
FIG. 4 is a diagram showing a schematic operational flowchart of blood pressure measurement performed by the appliance.

FIG. 4 shows a schematic operational flowchart of blood pressure measurement performed by the appliance 1. At the start of blood pressure measurement, the CPU 100 initializes the processing memory region and outputs a control signal to the valve driving circuit 330. Based on the control signal, the valve driving circuit 330 opens the valve 33 to discharge the air in the fluid bladder 22 of the belt 20. Next, control for adjusting the pressure sensor 31 to 0 mmHg is performed.

When blood pressure measurement is started, first, the CPU 100 closes the valve 33 via the valve driving circuit 330 and thereafter performs control for driving the pump 32 via the pump driving circuit 320 and sending air to the fluid bladder 21. Accordingly, the fluid bladder 21 is inflated so as to gradually increase the cuff pressure (step ST101 shown in FIG. 4).

When the cuff pressure is increased and reaches a predetermined pressure (YES in step ST102), the CPU 100 performs control for stopping the pump 32 via the pump driving circuit 320 and thereafter gradually releasing the valve 33 via the valve driving circuit 330. Accordingly, the fluid bladder 21 is contracted so as to gradually decrease the cuff pressure (step ST103).

Here, the predetermined pressure is a pressure that is sufficiently higher than the systolic blood pressure of the measurement subject (for example, systolic blood pressure+ 30 mmHg), and the predetermined pressure is stored in the memory 51 in advance or the CPU 100 determines the predetermined pressure by estimating the systolic blood pressure using a predetermined calculation method while the cuff pressure is increased (see, for example, JP 2001-70263A).

Also, for the pressure decrease speed, a target pressure decrease speed that is a target is set while the cuff pressure is increased, and the CPU 100 controls the opening degree of the valve 33 so as to reach the target pressure decrease speed (see JP 2001-70263A).

In the pressure decrease process, the pressure sensor 31 detects the pressure of the belt 20 and outputs a cuff pressure signal Pc. Based on the cuff pressure signal Pc, the CPU 100 calculates the blood pressure values (systolic blood pressure and diastolic blood pressure) by applying a known algorithm through the oscillometric method (step ST104). The CPU 100 also calculates the pulse based on the cuff pressure signal Pc. Note that the calculation of the blood pressure values and the pulse is not limited to being performed in the pressure decrease process, and may be performed in the pressure increase process.

Upon determining the blood pressure values by calculation (YES in step ST105), the CPU 100 performs first control for displaying, as the current blood pressure measurement information, the blood pressure values (see, for example, FIG. 23(A) described later) only on the first display device 50A (step ST106). Also, the CPU 100 performs control for storing the blood pressure values in the memory 51 (step ST107).

Upon completion of the measurement, the CPU 100 releases the valve 33 via the valve driving circuit 330 and performs control for discharging the air in the fluid bladder 21 of the belt 20 (step ST108). The blood pressure measurement (a blood pressure measurement period) thereby ends.

As described above, the CPU 100 displays the current blood pressure measurement information only on the first display device 50A (that is positioned so as to correspond to the volar-side surface 90a of the left wrist 90) during a blood pressure measurement period (first control). As used herein, the recommended blood pressure measurement posture refers to a posture in which the first display device 50A is facing the user's eyes. Accordingly, the user is prompted to view the current blood pressure measurement information (the blood pressure values in the above-described example) displayed on the first display device 50A while taking the recommended blood pressure measurement posture without performing an operation such as twisting the left wrist 90. Accordingly, the accuracy of blood pressure measurement is enhanced.

As used herein, "current blood pressure measurement information" does not include, for example, the blood pressure values obtained through blood pressure measurements performed in the past, information regarding functions other than the blood pressure measurement function (for example, the time obtained by the clock function, the value of body temperature measured by the body temperature measurement function, the value of activity amount measured by the activity amount measurement function, etc.), and the like.

On the other hand, during a period other than the blood pressure measurement period, the CPU 100 displays information that needs to be displayed (including information regarding blood pressure measurement) on the first display device 50A or the second display device 50B (second control). Accordingly, the display devices 50A and 50B are used to implement a plurality of functions including the blood pressure measurement function.

(Variation 1)

The flowchart in FIG. 7 described above is configured such that the processing is started in response to the user first taking the recommended blood pressure measurement posture (FIG. 6), but the configuration is not limited thereto. As shown in the flowchart in FIG. 11, the processing may be started after it is determined whether or not the posture of the user who is trying to take blood pressure measurement (the posture of the left wrist 90) matches the recommended blood pressure measurement posture (FIG. 6).

Figure 11:
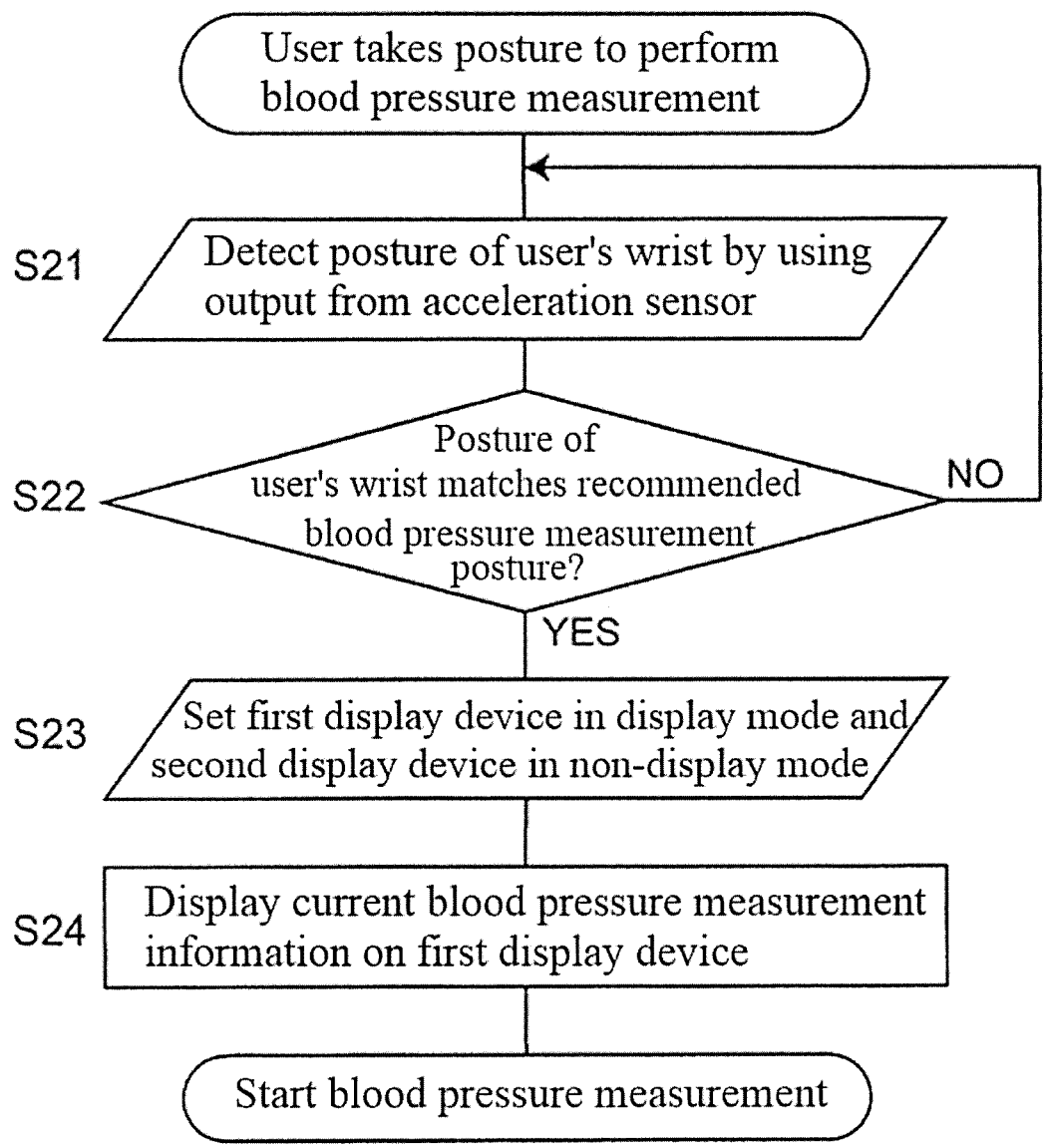
FIG. 11 is a diagram illustrating an operational flowchart of displaying current blood pressure measurement information during a period from when the user takes a posture for blood pressure measurement until the start of blood pressure measurement.

To be specific, as shown in step S21 in FIG. 11, the CPU 100 first detects the posture of the left wrist 90 of the user who is trying to take blood pressure measurement by using the output from the acceleration sensor 34. It is assumed at this point in time that the first display device 50A is in a non-display mode as shown in FIG. 8(A), and the second display device 50B is in a display mode that shows an indication N1 generated by the clock function and an indication N2 generated by the activity amount measurement function as shown in FIG. 8(B).

Next, the CPU 100 determines whether or not the posture of the left wrist 90 of the user matches the recommended blood pressure measurement posture (FIG. 6) (step S22 in FIG. 11). As used herein, "the posture of the left wrist 90" encompasses an inclination angle θ of the wrist (forearm) with respect to the table surface (horizontal surface) shown in FIG. 6 and an angular position φ of the volar-side surface about the wrist (see FIG. 5(A)). The CPU 100 waits for the posture of the left wrist 90 of the user to match the recommended blood pressure measurement posture (a return loop from NO in step S22 to step S21 in FIG. 11). Here, it is assumed that the inclination angle θ of the left wrist 90 has a pre-set acceptable angular range defined by a lower limit $θ_L$ and an upper limit $θ_U$. The acceptable angular range of the inclination angle θ will be expressed as $(θ_L, θ_U)$ where appropriate. Likewise, it is assumed that the angular position φ of the volar-side surface 90a about the left wrist 90 has a pre-set acceptable angular range (that is a range defined by a counter-clockwise limit angle $φ_L$ and a clockwise limit angle $φ_R$ as viewed from the user, where φ=0 when the volar-side surface 90a is facing immediately above, $φ_L<0$, and $φ_R>0$). The acceptable angular range of the angular position φ of the volar-side surface 90a about the left wrist 90 will be expressed as $(φ_L, φ_R)$ where appropriate. In this example, if the inclination angle θ of the left wrist 90 is within the acceptable angular range $(θ_L, θ_U)$ and the angular position φ of the volar-side surface 90a about the left wrist 90 is within the acceptable angular range $(φ_L, φ_R)$, it is determined that the posture of the left wrist 90 matches the recommended blood pressure measurement posture.

If it is determined that the posture of the left wrist 90 of the user matches the recommended blood pressure measurement posture (YES in step S22 in FIG. 11), the CPU 100 makes a transition to a start mode in which the CPU 100 functions as a starting unit and performs a preparation for starting the blood pressure measurement (a blood pressure measurement period). Then, as the preparation for starting the blood pressure measurement period, the CPU 100 sets the first display device 50A in a display mode and the second display device 50B in a non-display mode (step S23 in FIG. 11). Then, the CPU 100 displays the current blood pressure measurement information A on the first display device 50A (step S24 in FIG. 11). In this example, as shown in FIG. 9(A), as the current blood pressure measurement information, a drop down arrow mark M1 that indicates the blood pressure measurement is under preparation is displayed on the first display device 50A. On the other hand, as shown in FIG. 9(B), the second display device 50B goes blank. In this way, the CPU 100 displays the current blood pressure measurement information A only on the first display device 50A (first control). Through the preparation for starting the blood pressure measurement period, the blood pressure measurement (a blood pressure measurement period) is started, and the blood pressure measurement is performed in accordance with the flowchart shown in FIG. 4.

In this case, the preparation for starting the blood pressure measurement period is performed while the user is substantially taking the recommended blood pressure measurement posture. Through the preparation for starting the blood pressure measurement period, the blood pressure measurement period is started smoothly.

(Variation 2)

The flowchart in FIG. 11 described above is configured so as to automatically start a blood pressure measurement period through steps S23 and S24 if the posture of the user who is trying to take blood pressure measurement (the posture of the left wrist 90) matches the recommended blood pressure measurement posture (FIG. 6) (YES in step S22 in FIG. 11). However, the configuration is not limited thereto. As shown in the flowchart in FIG. 12, the following configuration is also possible in which the determination with respect to the posture of the left wrist 90 is performed in two steps: it is determined whether the posture of the left wrist 90 is within a first acceptable range of the recommended blood pressure measurement posture that is relatively broad; and it is determined whether the posture of the left wrist 90 is within a second acceptable range that is set within the first acceptable range, then, if it is determined that the posture of the left wrist 90 is within the first acceptable range, inquiry information inquiring whether or not to start a blood pressure measurement period is displayed.

In this example, the "first acceptable range" is set as a range enough to perform a preparation for starting the blood pressure measurement period. For the inclination angle θ of the left wrist 90, a first acceptable angular range defined by a lower limit $\theta_{L\ 1}$ and an upper limit $\theta_{U\ 1}$ is set. For the angular position φ of the volar-side surface 90a about the left wrist 90, a first acceptable angular range defined by a counter-clockwise limit angle $\varphi_{L\ 1}$ and a clockwise limit angle $\varphi_{R\ 1}$ is set. Likewise, the "second acceptable range" is set as a range that is more preferable to start the blood pressure measurement period. For the inclination angle θ of the left wrist 90, a second acceptable angular range defined by a lower limit $\theta_{L\ 2}$ and an upper limit $\theta_{U\ 2}$ is set. For the angular position φ of the volar-side surface 90a about the left wrist 90, a second acceptable angular range defined by a counter-clockwise limit angle $\varphi_{L\ 2}$ and a clockwise limit angle $\varphi_{R\ 2}$ is set. The set angular values satisfy the following relationships: $\theta_{L\ 1} \leq \theta_{L\ 2} < \theta_{U\ 2} \leq \theta_{U\ 1}$; and $\varphi_{L\ 1} \leq \varphi_{L\ 2} < 0 < j\varphi_{R\ 2} \leq \varphi_{R\ 1}$.

To be specific, it is assumed here that when the user takes a posture to perform blood pressure measurement in accordance with, for example, the instruction manual of the product, and at this time, the first display device 50A is set in a non-display mode as shown in FIG. 8(A), and an indication N1 generated by the clock function and an indication N2 generated by the activity amount measurement function are displayed on the second display device 50B as shown in FIG. 8(B).

Figure 12:
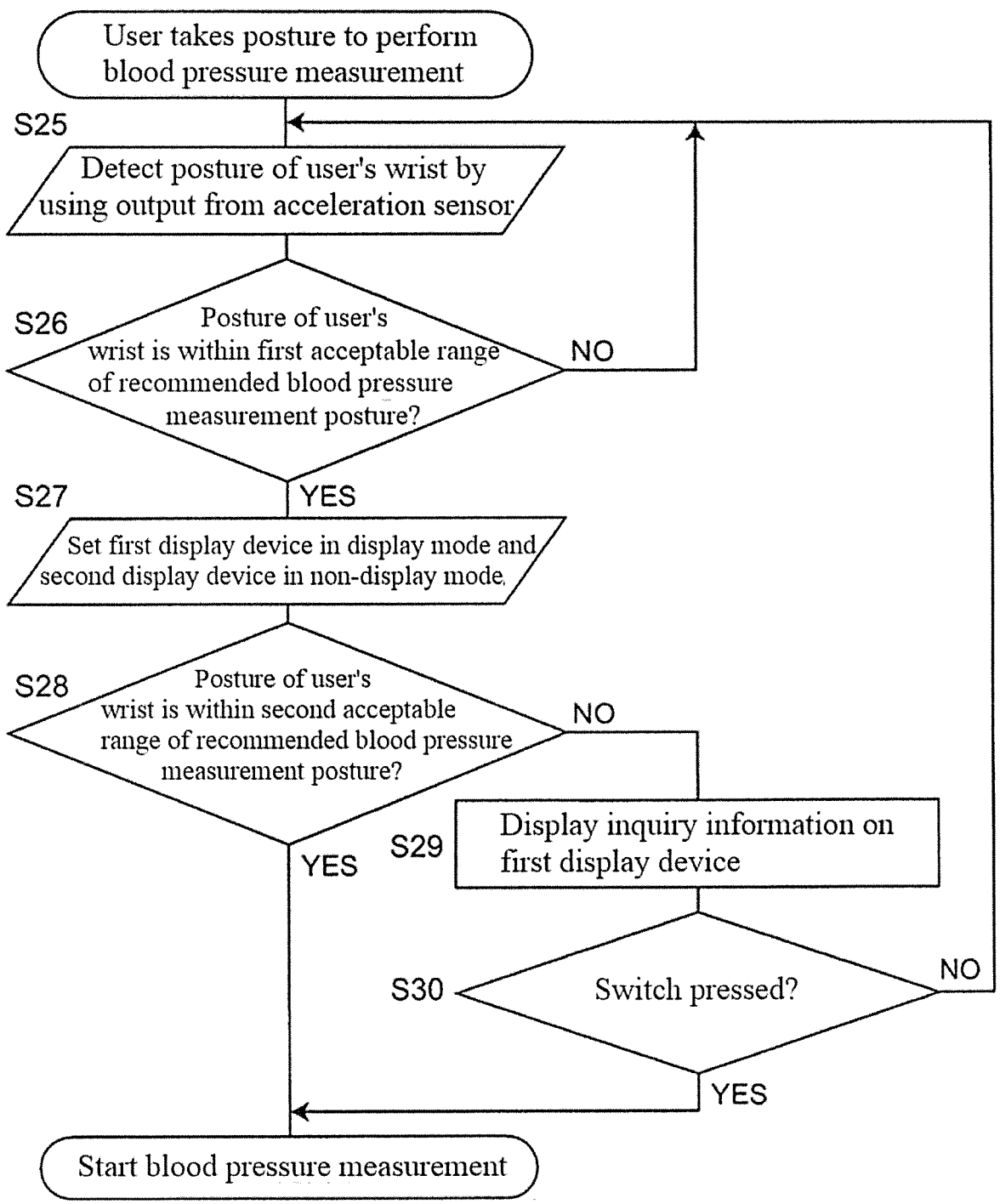
FIG. 12 is a diagram illustrating an operational flowchart of displaying inquiry information inquiring whether or not to start a blood pressure measurement period, performed during a period from when the user takes a posture for blood pressure measurement until the start of blood pressure measurement.

As shown in step S25 in FIG. 12, the CPU 100 detects the posture of the left wrist 90 of the user by using the output from the acceleration sensor 34, and then as shown in step S26 in FIG. 12, determines whether or not the posture of the left wrist 90 of the user is within the first acceptable range of the recommended blood pressure measurement posture (FIG. 6). To be specific, it is determined whether or not the inclination angle θ of the left wrist 90 is within the first acceptable angular range ($\theta_{L\ 1}$, $\theta_{U\ 1}$) and the angular position y of the volar-side surface 90a about the left wrist 90 is within the first acceptable angular range ($\varphi_{L\ 1}$, $\varphi_{R\ 1}$). The CPU 100 waits for the posture of the left wrist 90 of the user to be within the first acceptable range of the recommended blood pressure measurement posture (a return loop from NO in step S26 to step S25 in FIG. 12).

If it is determined that the posture of the left wrist 90 of the user is within the first acceptable range of the recommended blood pressure measurement posture (YES in step S26 in FIG. 12), the CPU 100 makes a transition to a start mode in which the CPU 100 functions as a starting unit and performs a preparation for starting the blood pressure measurement (a blood pressure measurement period). Then, the CPU 100 sets the first display device 50A in a display mode and the second display device 50B in a non-display mode, as the preparation for starting the blood pressure measurement period (step S27 in FIG. 12).

Next, as shown in step S28 in FIG. 12, the CPU 100 determines whether or not the posture of the left wrist 90 of the user is within the second acceptable range of the recommended blood pressure measurement posture that is smaller than the first acceptable range. To be specific, it is determined whether or not the inclination angle θ of the left wrist 90 is within the second acceptable angular range ($\theta_{L\ 2}$, $\theta_{U\ 2}$) and the angular position φ of the volar-side surface 90a about the left wrist 90 is within the second acceptable angular range ($\varphi_{L\ 2}$, $\varphi_{R\ 2}$).

If it is determined that the posture of the left wrist 90 of the user is within the second acceptable range of the recommended blood pressure measurement posture (YES in step S28 in FIG. 12), the CPU 100 ends the start mode and starts the blood pressure measurement (a blood pressure measurement period). In response thereto, the blood pressure measurement is performed in accordance with the flowchart shown in FIG. 4.

Figure 15A:
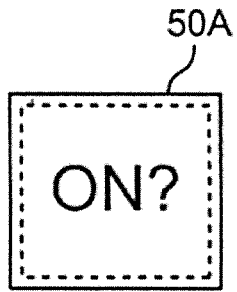
FIGS. 15(A) and 15(B) are diagrams showing display examples of the first display device and the second display device, respectively, during a period from when the user takes a posture for blood pressure measurement until the start of blood pressure measurement.
Figure 15B:
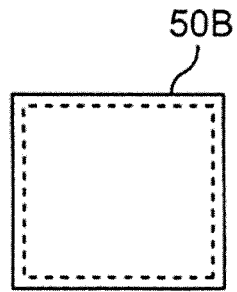

If, on the other hand, it is determined that the posture of the left wrist 90 of the user is within the first acceptable range of the recommended blood pressure measurement posture but is not within the second acceptable range, specifically, if it is determined that the inclination angle θ of the left wrist 90 is outside the second acceptable angular range ($\theta_{L\ 2}$, $\theta_{U\ 2}$), or the angular position φ of the volar-side surface 90a about the left wrist 90 is outside the second acceptable angular range ($\varphi_{L\ 2}$, $\varphi_{R\ 2}$), (NO in step S28 in FIG. 12), the CPU 100 displays, on the first display device 50A, inquiry information inquiring the user whether or not to start a blood pressure measurement period (step S29 in FIG. 12). In this example, as shown in FIG. 15(A), a character string of "ON?" is displayed on the first display device 50A as the inquiry information. On the other hand, the second display device 50B goes blank as shown in FIG. 15(B). In this way, during the start mode, the CPU 100 displays the inquiry information inquiring whether or not to start a blood pressure measurement period only on the first display device 50A (third control). Accordingly, upon looking at the inquiry information displayed on the first display device 50A, the user is prompted to make a decision as to whether or not to perform blood pressure measurement, or in other words, whether or not to start a blood pressure measurement period. If the user makes a decision to start a blood pressure measurement period, the user can, for example, input an instruction to start a blood pressure measurement period by pressing a push switch that serves as the first operation unit 52A provided on the main body 10A with the right hand (YES in step S30 in FIG. 12). With this configuration, the blood pressure measurement period is started according to the user's request. If an instruction to start a blood pressure measurement period is not input (NO in step S30 in FIG. 12), the CPU 100 repeats the processing from step S25 to step S30.

The flowchart shown in FIG. 12 is configured so as to make a transition to the start mode if it is determined that the posture of the left wrist 90 of the user is within the first acceptable range of the recommended blood pressure measurement posture (YES in step S26 in FIG. 12). However, the configuration is not limited thereto, and a configuration may also be used in which the transition to the start mode is made in response to the user pressing a push switch that serves as the first operation unit 52A provided on the main body 10A with the right hand. With this configuration, the preparation for starting the blood pressure measurement period can be performed according to the user's request.

(Variation 3)

The flowcharts in FIGS. 11 and 12 described above are configured such that the CPU 100 simply waits for the posture of the left wrist 90 of the user to match the recommended blood pressure measurement posture or to be within the first acceptable range of the recommended blood pressure measurement posture (the return loop from step S22 to step S21 in FIG. 11, and the return loop from NO in step S26 to step S25 in FIG. 12). However, the configuration is not limited thereto, and as shown in the flowchart in FIG. 13, a configuration may be used in which posture guidance information for guiding the user to take the recommended blood pressure measurement posture is displayed before the start of blood pressure measurement (a blood pressure measurement period).

To be specific, it is assumed here that when the user takes a posture to perform blood pressure measurement in accordance with, for example, the instruction manual of the product, and at this time, the first display device 50A is set in a non-display mode as shown in FIG. 8(A), and an indication N1 generated by the clock function and an indication N2 generated by the activity amount measurement function are displayed on the second display device 50B as shown in FIG. 8(B).

Figure 13:
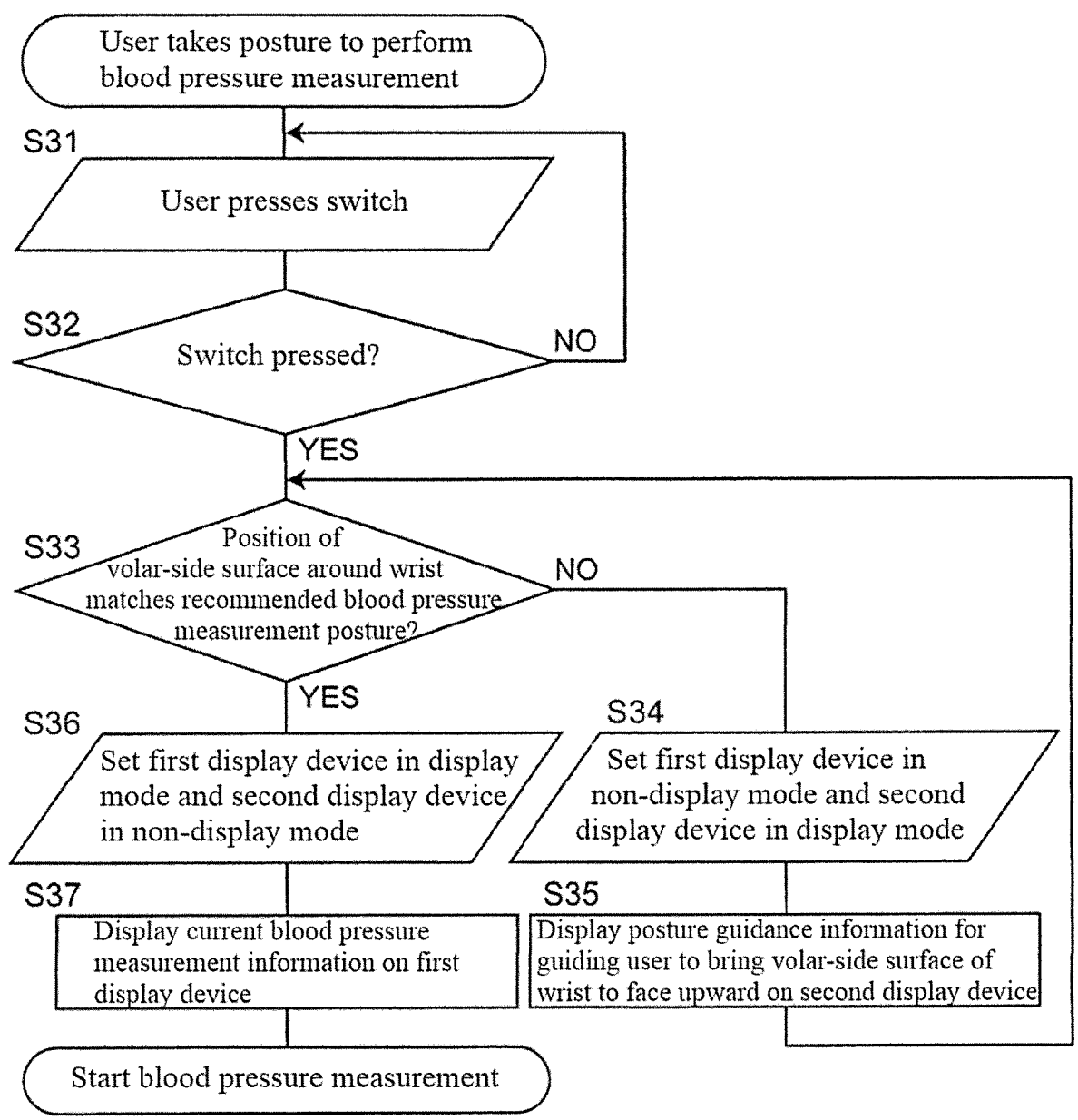
FIG. 13 is a diagram illustrating an operational flowchart of displaying posture guidance information, performed during a period from when the user takes a posture for blood pressure measurement until the start of blood pressure measurement.

In this state, as shown in step S31 of FIG. 13, if, for example, the user presses a push switch that serves as the first operation unit 52A provided on the main body 10A with the right hand (YES in step S32 in FIG. 13), as shown in step S33 of FIG. 13, the CPU 100 detects the posture of the left wrist 90 of the user who is trying to perform blood pressure measurement, in this example, in particular, the angular position φ of the volar-side surface 90a about the left wrist 90 by using the output from the acceleration sensor 34. Here, the CPU 100 detects whether or not the volar-side surface 90a of the left wrist 90 is facing upward. Then, the CPU 100 determines whether or not the angular position φ of the volar-side surface 90a about the left wrist 90 of the user matches the recommended blood pressure measurement posture (FIG. 6). To be specific, if the volar-side surface 90a of the left wrist 90 is facing upward (or in other words, the angular position φ of the volar-side surface 90a about the left wrist 90 is within the acceptable angular range ($φ_L$, $φ_R$)), it is determined that the posture matches the recommended blood pressure measurement posture. If, on the other hand, the volar-side surface 90a of the left wrist 90 is not facing upward (or in other words, the angular position φ of the volar-side surface 90a about the left wrist 90 is outside the acceptable angular range ($φ_L$, $φ_R$)), it is determined that the posture does not match the recommended blood pressure measurement posture.

Figure 10A:
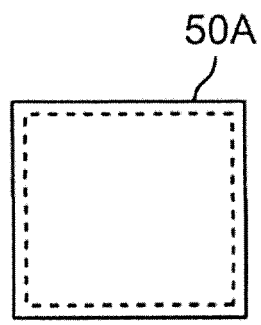
FIG. 10(A) is a diagram showing a display example of the first display device during a period from when the user takes a posture for blood pressure measurement until the start of blood pressure measurement.
Figure 10B:
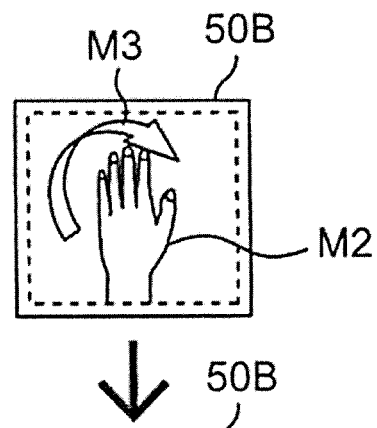
FIGS. 10(B) and 10(C) are display examples of the second display device during the period from when the user takes a posture for blood pressure measurement until the start of blood pressure measurement.
Figure 10C:
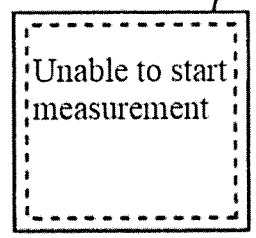

Here, if it is determined that the angular position φ of the volar-side surface 90a about the left wrist 90 of the user does not match the recommended blood pressure measurement posture (NO in step S33 in FIG. 13), the CPU 100 maintains the non-display mode of the first display device 50A (invisible from the user at this time) and the display mode of the second display device 50B (visible from the user at this time) (step S34 in FIG. 13). Next, in step S35 of FIG. 13, as shown in FIG. 10(B), the CPU 100 displays, in this example, on the second display device 50B, posture guidance information for guiding the user to bring the volar-side surface 90a of the left wrist 90 to face upward, in the form of an image (second control). The image shown in FIG. 10(B) includes an illustration M2 of the left hand (and the left wrist) and an arrow mark M3 for guiding the user to turn over the left hand (and the left wrist). Furthermore, after the image has been displayed, the CPU 100 displays a message "Unable to start measurement" on the second display device 50B as shown in FIG. 10(C). The image shown in FIG. 10(B) and the message shown in FIG. 10(C) may be repeatedly displayed at a regular interval (for example, at an interval of 0.5 seconds to several seconds). During a period in which FIGS. 10(B) and 10(C) are displayed on the second display device 50B, the first display device 50A is blank as shown in FIG. 10(A).

Looking at the image of FIG. 10(B) and the message of FIG. 10(C), the user can intuitively understand that he/she needs to turn over the left hand and the left wrist 90. That is, the user is prompted to take the recommended blood pressure measurement posture by turning over the left hand and the left wrist 90.

If it is determined that the angular position φ of the volar-side surface 90a about the left wrist 90 of the user matches the recommended blood pressure measurement posture (YES in step S33 in FIG. 13), the CPU 100 sets the first display device 50A in a display mode and the second display device 50B in a non-display mode (step S36 in FIG. 13), and then displays the current blood pressure measurement information on the first display device 50A (step S37 in FIG. 13). In this example, as shown in FIG. 9(A), a drop down arrow mark M1 is displayed on the first display device 50A as the current blood pressure measurement information, the drop down arrow mark M1 indicating that blood pressure measurement is under preparation. On the other hand, the second display device 50B goes blank as shown in FIG. 9(B). In this way, the CPU 100 displays the current blood pressure measurement information only on the first display device 50A (first control). The blood pressure measurement (a blood pressure measurement period) is thereby started, the blood pressure measurement is performed in accordance with the flowchart shown in FIG. 4.

With this configuration, the user takes the recommended blood pressure measurement posture, and thus the accuracy of blood pressure measurement is enhanced.

As the posture guidance information, a photographed image may be used instead of the illustration and the mark described above. It is also possible to use an animation or a video clip that shows the movement of the left hand (and the left wrist). The posture guidance information may include, not only a hand and/or a wrist, but also the upper part of the body. Also, the posture guidance information may be displayed not only on the second display device 50B, but also on the first display device 50A.

Also, the flowchart shown in FIG. 13 is configured such that as the posture of the left wrist 90 of the user, in particular, the angular position (of the volar-side surface 90a about the left wrist 90 is detected, but the configuration is not limited thereto. It is also possible to detect, as the posture of the left wrist 90 of the user, the inclination angle θ of the left wrist (forearm) 90 with respect to the table surface (horizontal surface). In this case, it is desirable that the CPU 100 determines whether or not the inclination angle θ of the left wrist 90 matches the recommended blood pressure measurement posture, and if it is determined that the inclination angle θ does not match the recommended blood pressure measurement posture, the CPU 100 displays posture guidance information for guiding the user to bring the inclination angle θ of the left wrist 90 to match the recommended blood pressure measurement posture on the first display device 50A or the second display device 50B.

A configuration is also possible in which an LED (Light Emitting Diode) is provided on the back side of the first display device 50A within the main body 10A or the back side of the second display device 50B within the main body 10B so that the CPU 100 can display the posture guidance information by illuminating or blinking the light of the LED (the light that has passed through the display screen of the first display device 50A or the second display device 50B). In this example, an LED 50C provided within the main body 10A is indicated by a dotted-line block in FIG. 3. For example, control is performed so as to illuminate or blink the LED 50C if the posture of the left wrist 90 of the user is out of the recommended blood pressure measurement posture, and to stop the illumination or blinking of the LED 50C if the posture of the left wrist 90 of the user matches the recommended blood pressure measurement posture. With this configuration, the user is prompted to bring the posture of the left wrist 90 to match the recommended blood pressure measurement posture in order to stop the illumination or blinking of the LED 50C. Instead of the above-described control, control may be performed so as to increase the blinking cycle of the LED 50C if the posture of the left wrist 90 of the user is brought away from the recommended blood pressure measurement posture, and to shorten the blinking cycle of the LED 50C if the posture of the left wrist 90 of the user is brought closer to the recommended blood pressure measurement posture. With this configuration, the user is promoted to bring the posture of the left wrist 90 to match the recommended blood pressure measurement posture in order to shorten the blinking cycle of the LED 50C.

(Variation 4)

The flowcharts in FIGS. 7, 11 and 13 described above are configured such that the processing is started after the appliance 1 has been attached to the left wrist 90 by the user, but the configuration is not limited thereto. A configuration is also possible in which detection is performed before the start of blood pressure measurement (a blood pressure measurement period) as to which of the left wrist and the right wrist the appliance 1 is attached to, and if it is determined that the appliance 1 is attached to the right wrist (unintended wrist), worn wrist guidance information for guiding the user to detach the appliance 1 from the right wrist and attach the appliance 1 to the left wrist (intended wrist) is displayed.

To be specific, it is assumed here that when the user takes a posture to perform blood pressure measurement in accordance with, for example, the instruction manual of the product, and at this time, the first display device 50A is set in a non-display mode as shown in FIG. 8(A), and an indication N1 generated by the clock function and an indication N2 generated by the activity amount measurement function are displayed on the second display device 50B as shown in FIG. 8(B).

Figure 14:
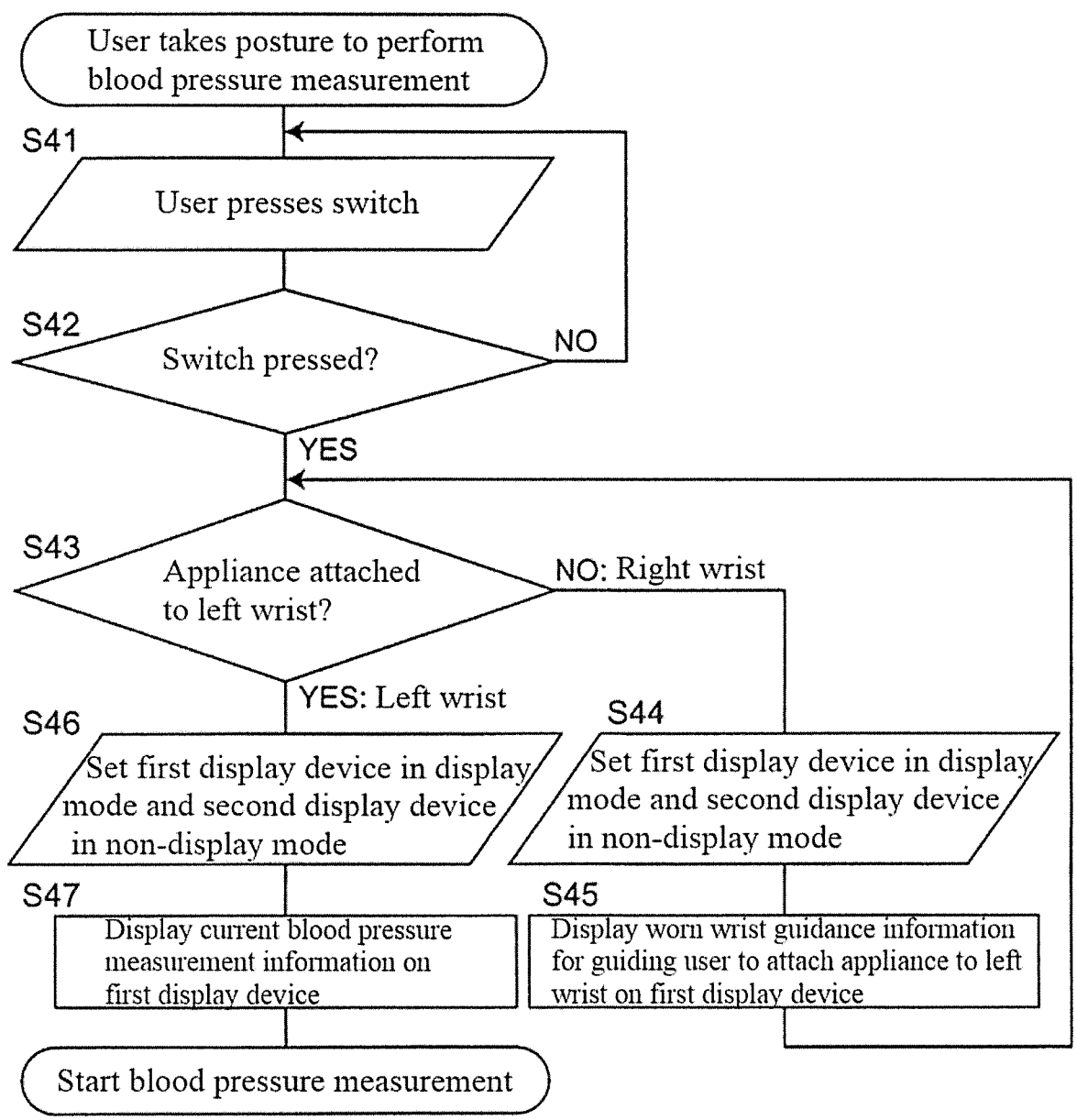
FIG. 14 is a diagram illustrating an operational flowchart of displaying worn wrist guidance information during a period from when the user takes a posture for blood pressure measurement until the start of blood pressure measurement.

In this state, as shown in step S41 of FIG. 14, if the user presses, for example, a push switch that serves as the first operation unit 52A provided on the main body 10A with the other hand (YES in step S42 in FIG. 14), as shown in step S43 of FIG. 14, the CPU 100 detects, by using the output from the acceleration sensor 34, which of the left wrist and the right wrist the appliance 1 is attached to, so as to determine whether or not the wrist to which the appliance 1 is attached is the left wrist 90.

Figure 16A:
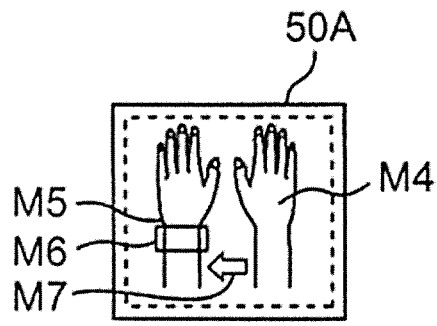
FIGS. 16(A) and 16(C) are diagrams showing display examples of the first display device during a period from when the user takes a posture for blood pressure measurement until the start of blood pressure measurement.
Figure 16B:
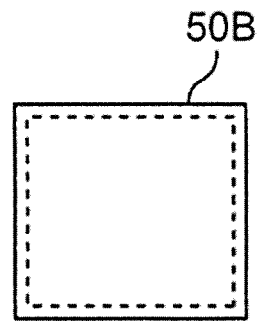
FIG. 16(B) is a diagram showing a display example of the second display device during the period from when the user takes a posture for blood pressure measurement until the start of blood pressure measurement.
Figure 16C:
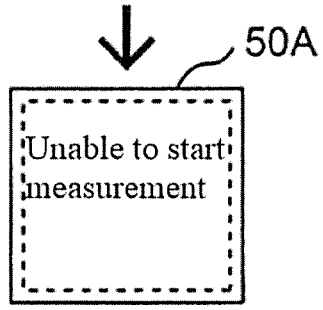

Here, if it is determined that the wrist to which the appliance 1 is attached is not the left wrist (NO in step S43 in FIG. 14), or in other words, if it is determined that the wrist to which the appliance 1 is attached is the right wrist, the CPU 100 sets the first display device 50A in a display mode (visible from the user at this time) and the second display device 50B in a non-display mode (invisible from the user at this time) (step S44 in FIG. 14). Next, in step S45 of FIG. 14, as shown in FIG. 16(A), in this example, the CPU 100 displays, on the first display device 50A, worn wrist guidance information for guiding the user to detach the appliance 1 from the right wrist and attach the appliance 1 to the left wrist 90, in the form of an image (second control). The image shown in FIG. 16(A) includes an illustration M4 of the right hand (and the right wrist), an illustration M5 of the left hand (and the left wrist), a rectangular mark M6 that indicates that the appliance 1 should be attached to the left wrist, and an arrow mark M7 pointing from the right toward the left. Furthermore, after the image has been displayed, the CPU 100 displays a message "Unable to start measurement" on the first display device 50A as shown in FIG. 16(C). The image shown in FIG. 16(A) and the message shown in FIG. 16(C) may be repeatedly displayed at a regular interval (for example, at an interval of 0.5 seconds to several seconds). During a period in which FIGS. 16(A) and 16(C) are displayed on the first display device 50A, the second display device 50B is blank as shown in FIG. 16(B).

The user can intuitively understand that he/she has to attach the appliance 1 to the left wrist 90 by looking at the image shown in FIG. 16(A) and the message shown in FIG. 16(C). That is, the user is prompted to detach the appliance 1 from the right wrist and attach the appliance 1 to the left wrist 90.

If it is determined that the wrist to which the appliance 1 is attached is the left wrist (YES in step S43 in FIG. 14), the CPU 100 sets the first display device 50A in a display mode and the second display device 50B in a non-display mode (step S46 in FIG. 14), and then displays the current blood pressure measurement information on the first display device 50A (step S47 in FIG. 14). In this example, as shown in FIG. 9(A), a drop down arrow mark M1 that indicates that blood pressure measurement is under preparation is displayed on the first display device 50A as the current blood pressure measurement information. On the other hand, as shown in FIG. 9(B), the second display device 50B goes blank. In this way, the CPU 100 displays the current blood pressure measurement information only on the first display device 50A (first control). The blood pressure measurement (a blood pressure measurement period) is thereby started, and the blood pressure measurement is performed in accordance with the flowchart shown in FIG. 4.

In this case, blood pressures are measured in the left wrist 90, and thus the accuracy of blood pressure measurement is enhanced.

Figure 17A:
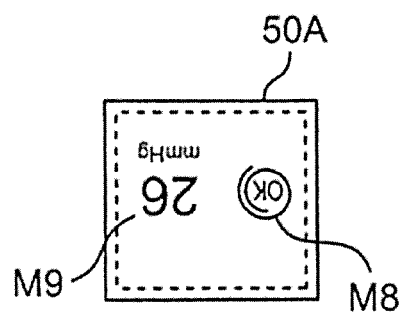
FIGS. 17(A) and 17(B) are diagrams showing display examples of the first display device and the second display device, respectively, during a period from when the user takes a posture for blood pressure measurement until the start of blood pressure measurement.
Figure 17B:
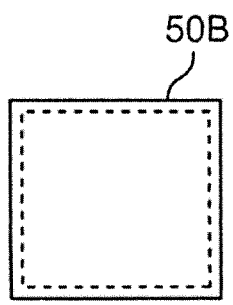

The worn wrist guidance information for guiding the user to attach the appliance 1 to the left wrist 90 is not limited to those shown in FIGS. 16(A) and 16(C). For example, as shown in FIG. 17(A), as the worn wrist guidance information, an image including a mark M8 that indicates "OK" encircled by a spiral line shown in an inverted manner and a mark M9 that indicates "26 mmHg" as the pressure shown in an inverted manner may be displayed. Looking at the image, the user is prompted to detach the appliance 1 from the right wrist and attach the appliance 1 to the left wrist 90. During a period in which FIG. 17(A) is displayed on the first display device 50A, the second display device 50B is blank as shown in FIG. 17(B).

As the worn wrist guidance information, an animation or a video clip that shows an operation of detaching the appliance 1 from the right wrist and then attaching the appliance 1 to the left wrist may be used instead of the illustration and the marks described above. The worn wrist guidance information may include, not only a hand and/or a wrist, but also the upper part of the body. Also, the worn wrist guidance information may be displayed not only on the first display device 50A, but also on the second display device 50B.

A configuration is also possible in which an LED (for example, an LED 50C incorporated in the main body 10A shown in FIG. 3) is provided on the back side of the first display device 50A within the main body 10A or the back side of the second display device 50B within the main body 10B so that the CPU 100 can display the worn wrist guidance information by illuminating or blinking the light of the LED (the light that has passed through the display screen of the first display device 50A or the second display device 50B). For example, control is performed so as to illuminate or blink the LED 50C if the wrist to which the appliance 1 is attached is the right wrist (unintended wrist), and to stop the illumination or blinking of the LED 50C if the wrist to which the appliance 1 is attached is the left wrist (intended wrist). With this configuration, the user is prompted to attach the appliance 1 to the intended wrist in order to stop the illumination or blinking of the LED 50C.

(Variation 5)

Figure 18A:
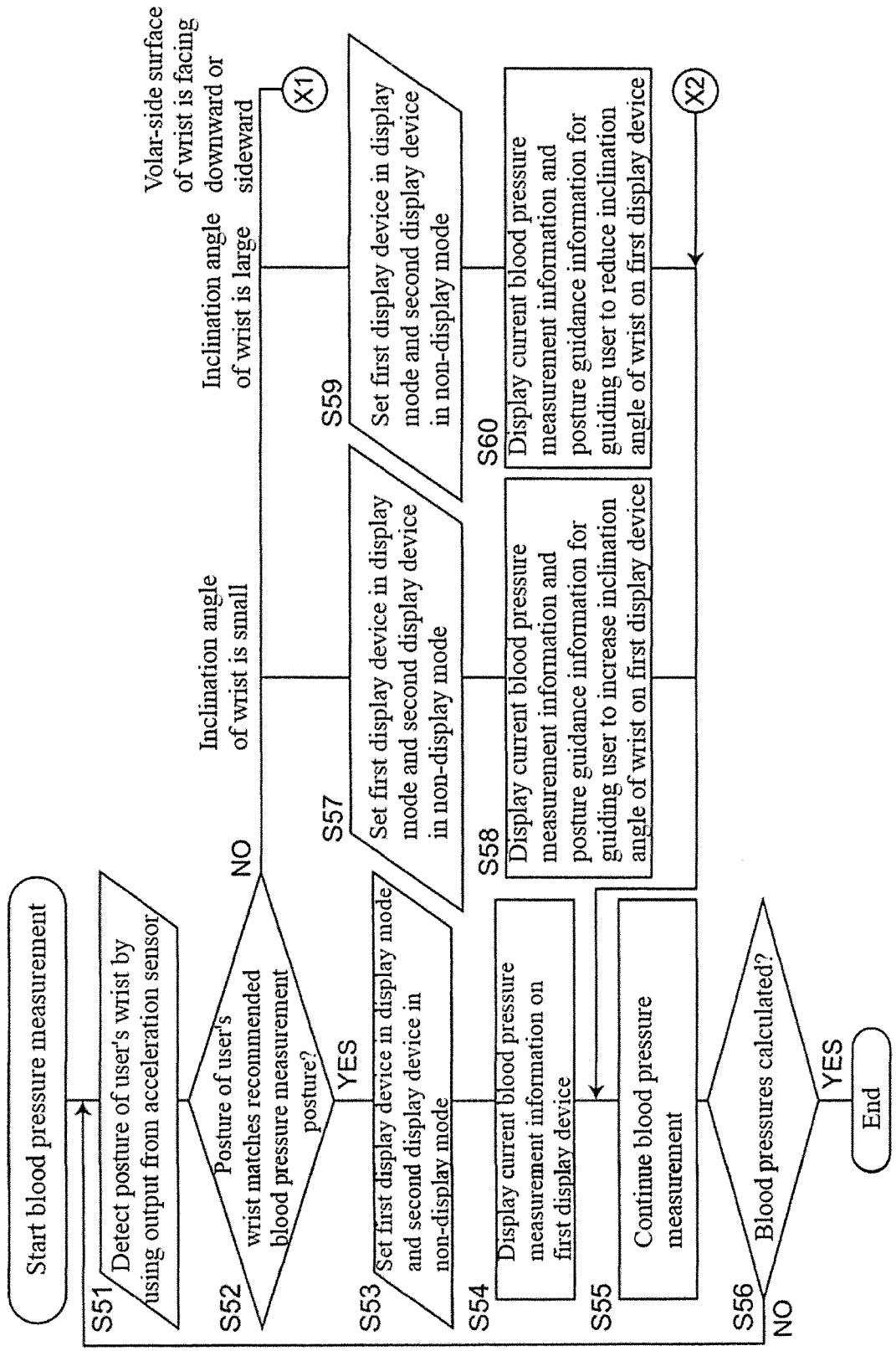
FIG. 18(A) is a diagram showing an operational flowchart of displaying posture guidance information that is executed in parallel to the overall operational flowchart shown in FIG. 4 during blood pressure measurement.
Figure 18B:
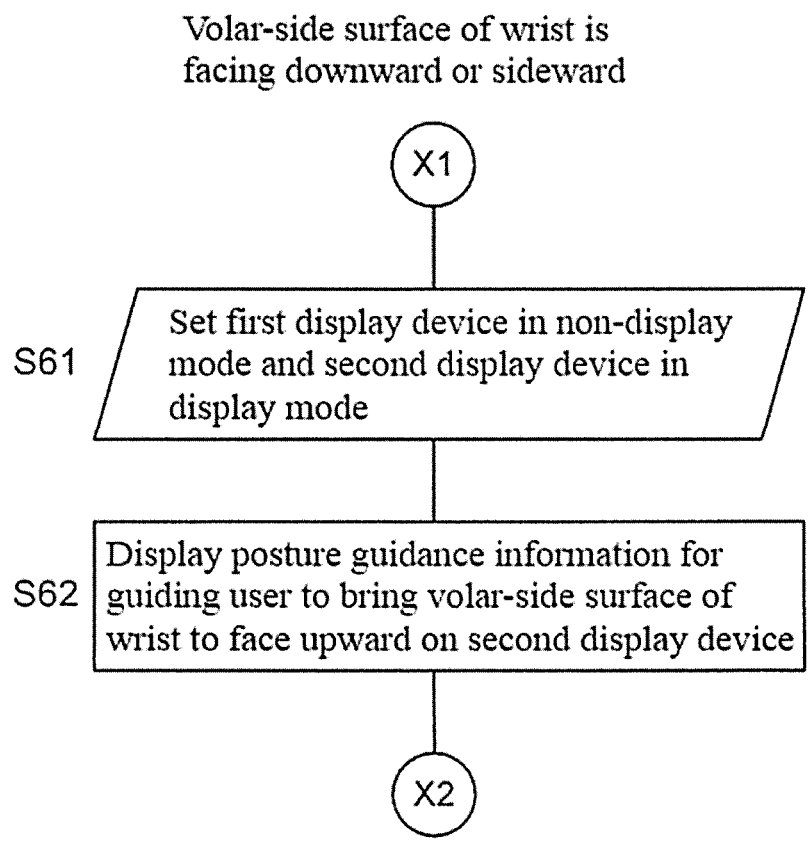
FIG. 18(B) is a diagram showing an operational flowchart of displaying posture guidance information that is executed together with the flowchart shown in FIG. 18(A) in parallel to the overall operational flowchart shown in FIG. 4 during blood pressure measurement.

The flowchart in FIG. 13 described above is configured such that the posture guidance information is displayed before the start of blood pressure measurement, but the configuration is not limited thereto. As shown in a flowchart in FIGS. 18(A) and 18(B), the posture guidance information may be displayed during blood pressure measurement (a blood pressure measurement period). FIGS. 18(A) and 18(B) show a flowchart of displaying posture guidance information that is executed in parallel to the overall operational flowchart shown in FIG. 4 during blood pressure measurement.

It is assumed here that as the current blood pressure measurement information, a drop down arrow mark M1 that indicates that blood pressure measurement is under preparation is displayed on the first display device 50A at the start of blood pressure measurement as shown in FIG. 9(A), and the second display device 50B is blank as shown in FIG. 9(B).

During blood pressure measurement, the CPU 100 detects, by using the output from the acceleration sensor 34, the posture of the left wrist 90 of the user during blood pressure measurement, specifically in this example, the inclination angle $\theta$ of the left wrist (forearm) 90 with respect to the table surface (horizontal surface), and the angular position $\varphi$ of the volar-side surface 90a about the left wrist 90 (whether or not the volar-side surface 90a is facing upward) as shown in step S51 in FIG. 18(A). Then, the CPU 100 determines whether or not the posture of the left wrist 90 of the user matches the recommended blood pressure measurement posture (FIG. 6) as shown in step S52 in FIG. 18(A).

To be specific, if the inclination angle $\theta$ of the left wrist (forearm) 90 is within a pre-set acceptable angular range ($\theta_L$, $\theta_U$), and the volar-side surface 90a of the left wrist 90 is facing upward (or in other words, if the angular position $\varphi$ of the volar-side surface 90a is within an acceptable angular range ($\varphi_L$, $\varphi_R$)), it is determined that the posture of the left wrist 90 of the user matches the recommended blood pressure measurement posture. Otherwise, for example, if the inclination angle $\theta$ of the left wrist 90 is less than the lower limit $\theta_L$, if the inclination angle $\theta$ of the left wrist 90 is greater than the upper limit $\theta_U$, or if the volar-side surface 90a of the left wrist 90 is facing downward or sideward rather than upward, (or in other words, if the angular position $\varphi$ of the volar-side surface 90a is outside the acceptable angular range ($\varphi_L$, $\varphi_R$)), it is determined that the posture of the left wrist 90 of the user does not match the recommended blood pressure measurement posture.

Figure 19A:
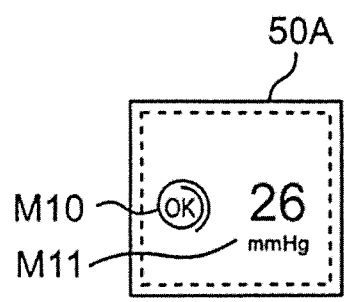
FIGS. 19(A) and 19(B) are diagrams showing display examples of the first display device and the second display device, respectively, during a blood pressure measurement period.
Figure 19B:
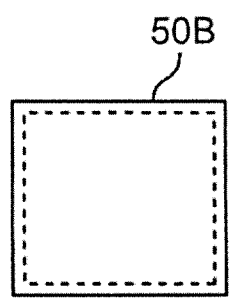

If it is determined that the posture of the left wrist 90 of the user matches the recommended blood pressure measurement posture (YES in step S52 in FIG. 18(A)), the CPU 100 sets the first display device 50A in a display mode and the second display device 50B in a non-display mode (step S53 in FIG. 18(A)), and then displays the current blood pressure measurement information on the first display device 50A (step S54 in FIG. 18(A)). In this example, as shown in FIG. 19(A), as the current blood pressure measurement information, an image including a mark M10 that indicates "OK" encircled by a spiral line and a mark M11 that indicates "26 mmHg" as the pressure is displayed on the first display device 50A. The mark M10 indicates that the belt 20 is properly wound around the left wrist 90. The mark M11 indicates the current cuff pressure. As shown in FIG. 19(B), the second display device 50B goes blank. In this way, the CPU 100 displays the current blood pressure measurement information only on the first display device 50A (first control). In this state, the processing of blood pressure measurement is continued (step S55 in FIG. 18(A)), and then blood pressures are calculated (step S56 in FIG. 18(A)).

Figure 20A:
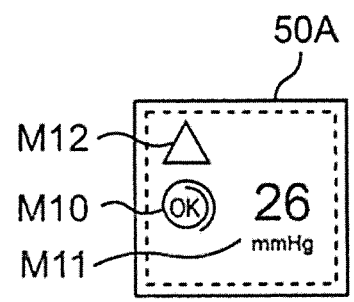
FIGS. 20(A) and 20(B) are diagrams showing display examples of the first display device and the second display device, respectively, during a blood pressure measurement period.
Figure 20B:
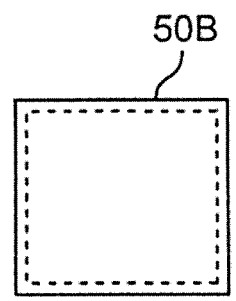

If, on the other hand, it is determined that the posture of the left wrist 90 of the user does not match the recommended blood pressure measurement posture (NO in step S52 in FIG. 18(A)), and the inclination angle $\theta$ of the left wrist 90 is less than the lower limit $\theta_L$, for example, the CPU 100 sets the first display device 50A in a display mode and the second display device 50B in a non-display mode (step S57 in FIG. 18(A)). Next, in step S58 in FIG. 18(A), the CPU 100 displays the current blood pressure measurement information on the first display device 50A (first control), and also displays posture guidance information for guiding the user to increase the inclination angle $\theta$ of the left wrist 90 on the first display device 50A (fourth control). In this example, as shown in FIG. 20(A), an image including, in addition to a mark M10 that indicates "OK" encircled by a spiral line and a mark M11 that indicates "26 mmHg" as the pressure that serve as the current blood pressure measurement information, an up triangular mark M12 provided above the mark M10 (encircled by a spiral line) is displayed as the posture guidance information on the first display device 50A. The up triangular mark M12 intuitively informs the user to increase the inclination angle $\theta$ of the left wrist 90. Looking at the information displayed on the first display device 50A, the user is prompted to increase the inclination angle $\theta$ of the left wrist 90. As a result of the guidance, in steps S55 and S56 in FIG. 18(A), blood pressures are measured with an appropriate inclination angle $\theta$, and thus the accuracy of blood pressure measurement is enhanced. During a period in which FIG. 20(A) is displayed on the first display device 50A, the second display device 50B is blank as shown in FIG. 20(B).

Figure 21A:
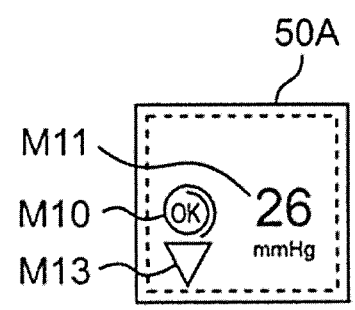
FIGS. 21(A) and 21(B) are diagrams showing display examples of the first display device and the second display device, respectively, during a blood pressure measurement period.
Figure 21B:
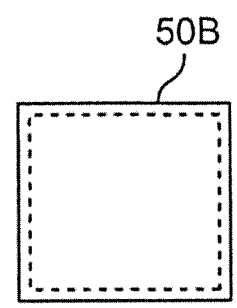

If it is determined that the posture of the left wrist 90 of the user does not match the recommended blood pressure measurement posture (NO in step S52 in FIG. 18(A)) and the inclination angle θ of the left wrist 90 is greater than the upper limit $θ_U$, the CPU 100 sets the first display device 50A in a display mode and the second display device 50B in a non-display mode (step S59 in FIG. 18(A)). Next, in step S60 in FIG. 18(A), the CPU 100 displays the current blood pressure measurement information on the first display device 50A (first control) and also displays posture guidance information for guiding the user to reduce the inclination angle θ of the left wrist 90 on the first display device 50A (fourth control). In this example, as shown in FIG. 21(A), an image including, in addition to a mark M10 that indicates "OK" encircled by a spiral line and a mark M11 that indicates "26 mmHg" as the pressure that serve as the current blood pressure measurement information, a down triangular mark M13 provided below the mark M10 (encircled by a spiral line) is displayed as the posture guidance information on the first display device 50A. The down triangular mark M13 intuitively informs the user to reduce the inclination angle θ of the left wrist 90. Looking at the image displayed on the first display device 50A, the user is prompted to reduce the inclination angle θ of the left wrist 90. As a result of the guidance, in steps S55 and S56 in FIG. 18(A), blood pressures are measured with an appropriate inclination angle θ, and thus the accuracy of blood pressure measurement is enhanced. During a period in which FIG. 21(A) is displayed on the first display device 50A, the second display device 50B is blank as shown in FIG. 21(B).

If it is determined that the posture of the left wrist 90 of the user does not match the recommended blood pressure measurement posture (NO in step S52 in FIG. 18(A)) and the volar-side surface 90a of the left wrist 90 is facing downward or sideward rather than upward (or in other words, the angular position φ of the volar-side surface 90a is outside the acceptable angular range ($φ_L$, $φ_R$)), the CPU 100 sets the first display device 50A in a non-display mode (invisible from the user at this time) and the second display device 50B in a display mode (visible from the user at this time) (step S61 in FIG. 18(B)). Then, in step S62 in FIG. 18(B), the CPU 100 displays posture guidance information for guiding the user to bring the volar-side surface 90a of the left wrist 90 to face upward in the form of an image on the second display device 50B as shown in FIG. 10(B) (fourth control). As already described, the image shown in FIG. 10(B) includes the illustration M2 of the left hand (and the left wrist) and the arrow mark M3 for guiding the user to turn over the left hand (and the left wrist). Looking at the image shown in FIG. 10(B), the user can intuitively understand that he/she needs to turn over the left hand and the left wrist 90. That is, the user is prompted to turn over the left hand and the left wrist 90. As a result of the guidance, in steps S55 and S56 shown in FIG. 18(A), blood pressures are measured while the user is taking an appropriate posture in which the volar-side surface 90a of the left wrist 90 is facing upward, and thus the accuracy of blood pressure measurement is enhanced. During a period in which FIG. 10(B) is displayed on the second display device 50B, the first display device 50A is blank as shown in FIG. 10(A).

In step S52 shown in FIG. 18(A), if it is determined that the inclination angle θ of the left wrist (forearm) 90 is outside the pre-set acceptable angular range ($θ_L$, $θ_U$) and the volar-side surface 90a of the left wrist 90 is facing downward or sideward, the CPU 100 performs, for example, one of the following processing operations: processing of guiding the user to bring the inclination angle θ within the acceptable angular range ($θ_L$, $θ_U$) (steps S57 and S58 or steps S59 and S60 shown in FIG. 18(A)); and processing of guiding the user to bring the volar-side surface 90a to face upward (steps S61 and S62 shown in FIG. 18(B)), and thereafter performs the other processing. Alternatively or in addition thereto, the CPU 100 may set both the first display device 50A and the second display device 50B in a display mode, and perform in parallel the processing of guiding the user to bring the inclination angle θ within the acceptable angular range ($θ_L$, $θ_U$) (step S58 or S60 shown in FIG. 18(A)) and the processing of guiding the user to bring the volar-side surface 90a to face upward (step S62 shown in FIG. 18(B)).

Furthermore, the CPU 100 may display the above-described worn wrist guidance information (for example, FIGS. 16(A) and 16(C)) on the first display device 50A or the second display device 50B during blood pressure measurement (a blood pressure measurement period) (fifth control). With this configuration, the user can intuitively understand that he/she needs to attach the appliance 1 to the left wrist 90 by looking at the image shown in FIG. 16(A) and the message shown in FIG. 16(C). That is, the user is prompted to detach the appliance 1 from the right wrist and then attach the appliance 1 to the left wrist 90. The display of the worn wrist guidance information during a blood pressure measurement period has significance particularly when blood pressure measurement processing is started without performing detection as to which of the left wrist and the right wrist the appliance 1 is attached to (for example, when blood pressure measurement processing is started based on the flowchart shown in FIG. 7).

(Variation 6)

FIG. 22(A) to FIG. 23(D) show various examples of images that show "ongoing blood pressure measurement information" displayed on the first display device 50A during a blood pressure measurement period from the start of blood pressure measurement to the completion of the blood pressure measurement.

Figure 22A:
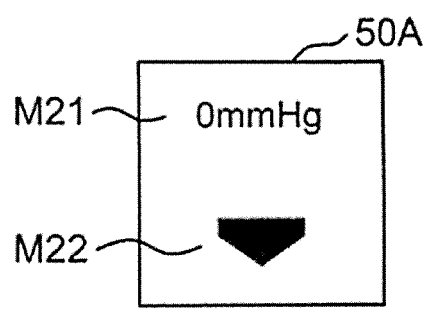
FIGS. 22(A) and 22(B) are diagrams showing display examples of the first display device at the start of blood pressure measurement.
Figure 22B:
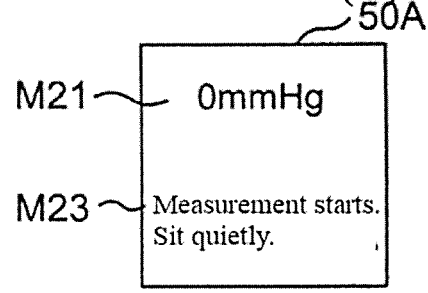

FIG. 22(A) and FIG. 22(B) are display examples shown at the start of blood pressure measurement. FIG. 22(A) shows an image including an indication M21 that indicates "0 mmHg" as the cuff pressure at the start of blood pressure measurement and a drop down arrow mark M22 that indicates that blood pressure measurement is under preparation. FIG. 22(B) shows an image including an indication M21 that indicates "0 mmHg" as the cuff pressure at the start of blood pressure measurement and a message M23 "Measurement starts. Sit quietly" that is an instruction (advice) for the user.

Figure 22C:
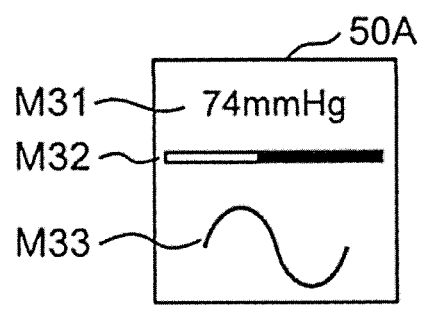
FIGS. 22(C), 22(D), and 22(E) are diagrams showing display examples of the first display device during blood pressure measurement.
Figure 22D:
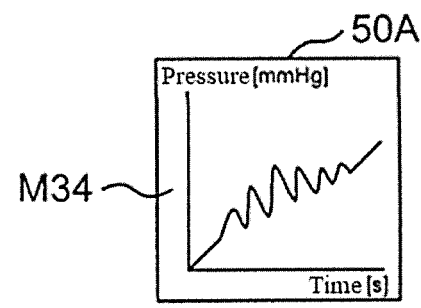
Figure 22E:
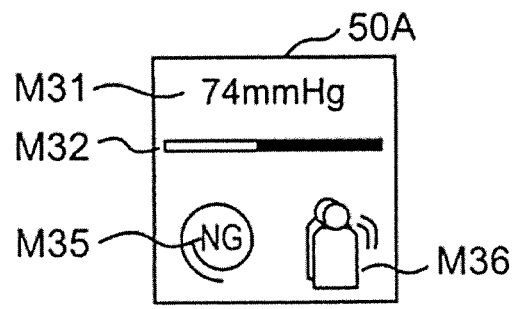

FIGS. 22(C), 22(D) and 22(E) are display examples shown during blood pressure measurement. FIG. 22(C) shows an image including an indication M31 that indicates "74 mmHg" as the current cuff pressure during blood pressure measurement, a strip graph M32 that shows the progress of blood pressure measurement, and a sinusoidal waveform M33 that indicates that the pulse is being detected (illuminated each time the pulse is detected). FIG. 22(D) shows an image including a pressure waveform graph M34 during blood pressure measurement, with measurement time (expressed in sec) on the horizontal axis and pressure (cuff pressure) (expressed in mmHg) on the vertical axis. FIG. 22(E) shows an indication M31 that indicates "74 mmHg" as the current cuff pressure during blood pressure measurement, a strip graph M32 that shows the progress of blood pressure measurement, a mark M35 that indicates "NG"

(i.e., the belt is loose) encircled by a spiral line, and a mark M36 that indicates that the body (or arm) is moving. The marks M35 and M36 are information regarding the reliability of the blood pressure measurement performed.

Figure 23A:
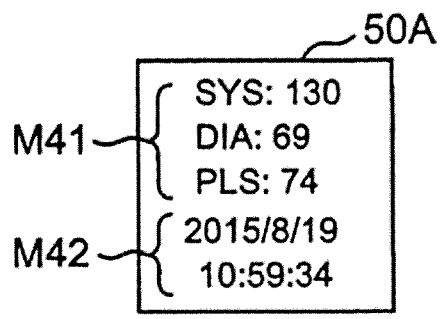
FIGS. 23(A), 23(B), 23(C), and 23(D) are diagrams showing display examples of the first display device at the end of blood pressure measurement.
Figure 23B:
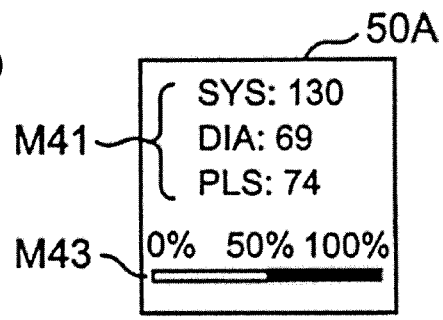
Figure 23C:
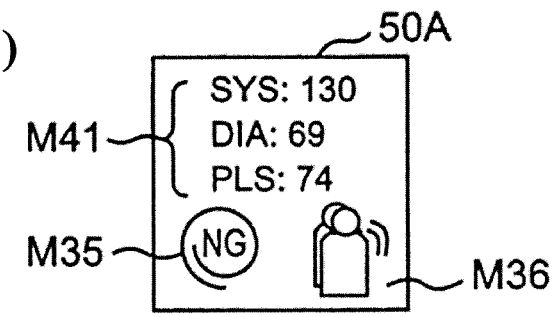
Figure 23D:
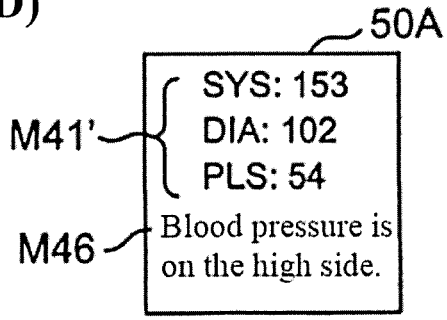

FIGS. 23(A), 23(B), 23(C), and 23(D) are display examples shown at the end of blood pressure measurement. FIG. 23(A) shows an image including an indication M41 that indicates "SYS: 130" as the systolic blood pressure (highest blood pressure), "DIA: 69" as the diastolic blood pressure (lowest blood pressure), and "PLS: 74" as the pulse obtained through the blood pressure measurement, as well as an indication M42 that indicates "2015/8/19" and "10:59:34" as the date and time at which the blood pressure measurement was performed. The systolic blood pressure and the diastolic blood pressure are expressed in units of "mmHg", and the pulse is expressed in units of "beats/min". FIG. 23(B) shows an image including an indication M41 that indicates "SYS: 130" as the systolic blood pressure, "DIA: 69" as the diastolic blood pressure, and "PLS: 74" as the pulse obtained through the blood pressure measurement, as well as a strip graph M43 that shows the percentage (%) of achievement with respect to the number of times of measurement performed in a set period (for example, in one month) including the time at which the blood pressure measurement was performed. FIG. 23(C) shows an image including an indication M41 that indicates "SYS: 130" as the systolic blood pressure, "DIA: 69" as the diastolic blood pressure, and "PLS: 74" as the pulse obtained through the blood pressure measurement, a mark M35 that indicates "NG" (i.e., the belt is loose) encircled by a spiral line, and a mark M36 that indicates that the body (or arm) is moving. As already described, the marks M35 and M36 are information regarding the reliability of the blood pressure measurement performed. FIG. 23(D) shows an image including an indication M41' that indicates "SYS: 153" as the systolic blood pressure (highest blood pressure), "DIA: 102" as the diastolic blood pressure (lowest blood pressure), and "PLS: 54" as the pulse obtained through the blood pressure measurement, and a message M46 "Blood pressure is on the high side" that is an evaluation of blood pressure values obtained through the blood pressure measurement.

As described above, during a blood pressure measurement period, various types of information may be displayed on the first display device 50A as the "ongoing blood pressure measurement information".

(Variation 7)

Figure 25A:
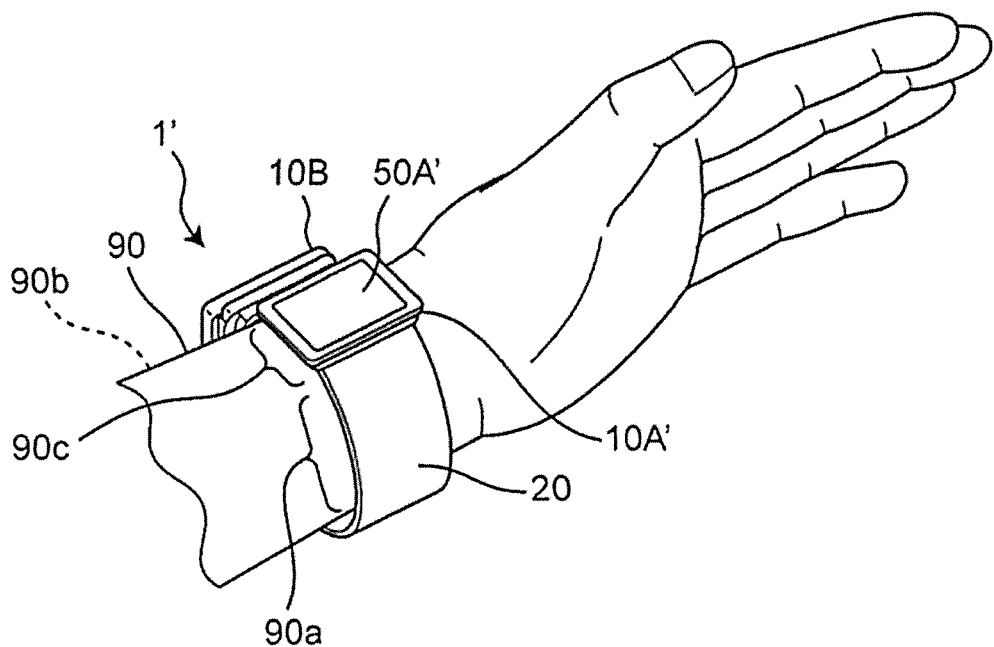
FIG. 25(A) is a diagram showing an appliance according to a variation that is wound around the user's left wrist (radius-side surface).
Figure 25B:
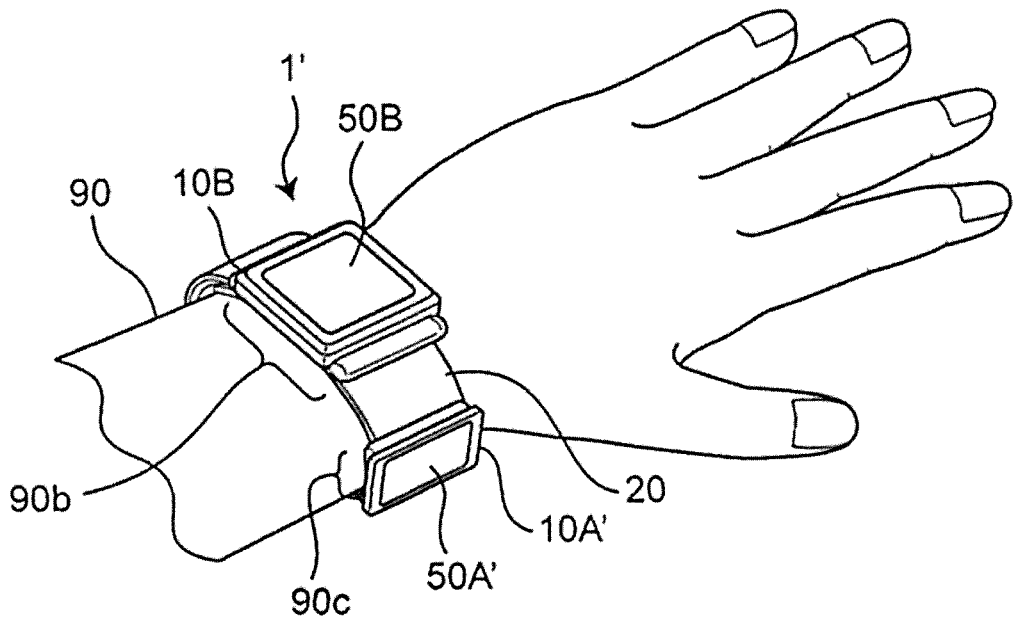
FIG. 25(B) is a diagram showing the appliance according to a variation that is wound around the user's left wrist (back-side surface).

The appliance 1 described above is configured such that the first display device 50A (and the main body 10A) is positioned so as to correspond to the volar-side surface 90a of the left wrist 90 as shown in FIG. 5(A), and the second display device 50B (and the main body 10B) is positioned so as to correspond to the back-side surface 90b of the left wrist 90 as shown in FIG. 5(B). However, the configuration is not limited thereto. For example, it is possible to use a configuration in which a first display device 50A' (and a main body 10A') is positioned so as to correspond to a radius-side surface (the surface of the thumb-side portion of the outer circumference of the wrist) 90c of the left wrist 90 as shown in FIG. 25(A), and a second display device 50B (and a main body 10B) is positioned so as to correspond to the back-side surface 90b of the left wrist 90 as shown in FIG. 25(B). This will be referred to as "appliance 1'".

Figure 24A:
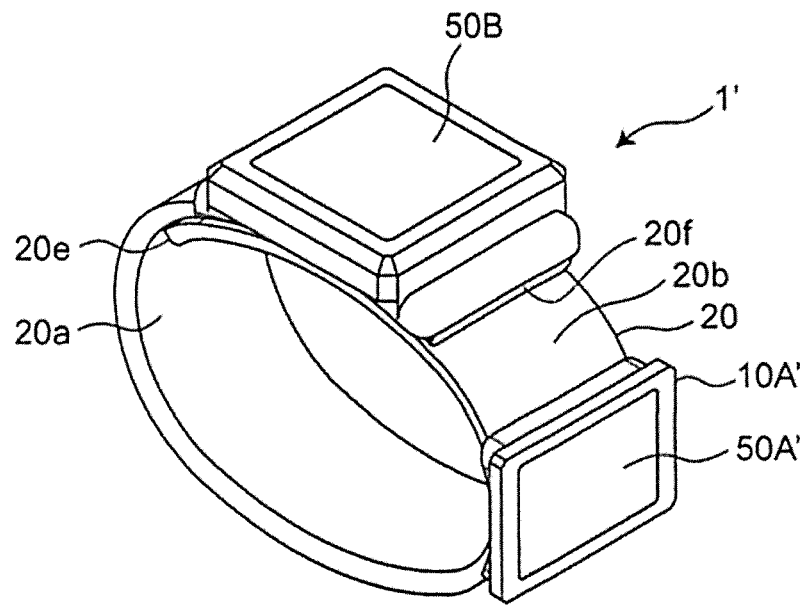
FIG. 24(A) is a perspective view of an external appearance of an appliance according to a variation.
Figure 24B:
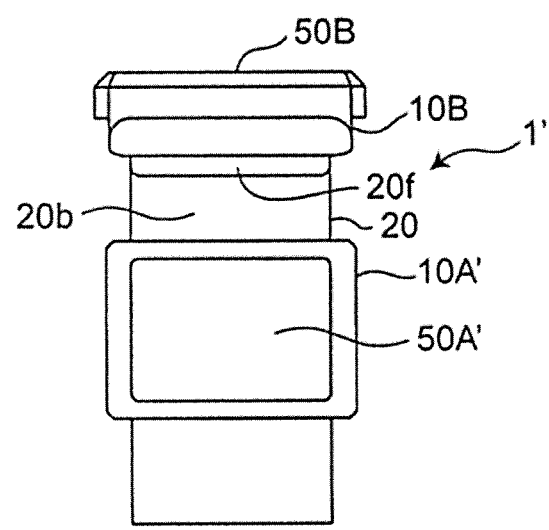
FIG. 24(B) is a right side view of the appliance shown in FIG. 24(A).
Figure 24C:
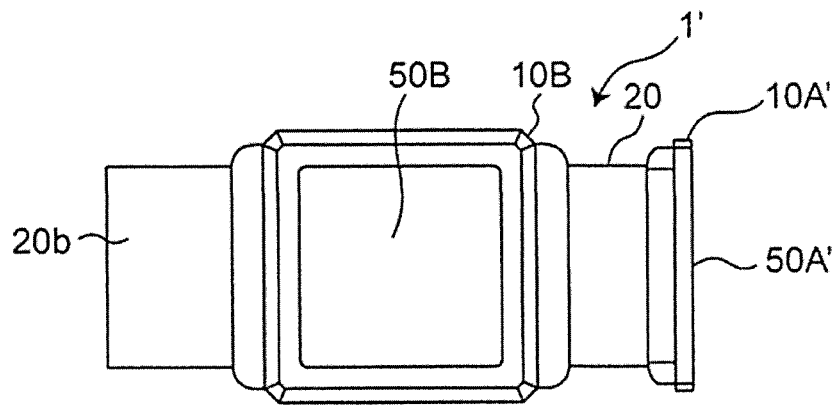
FIG. 24(C) is a top view of the appliance shown in FIG. 24(A).
Figure 24D:
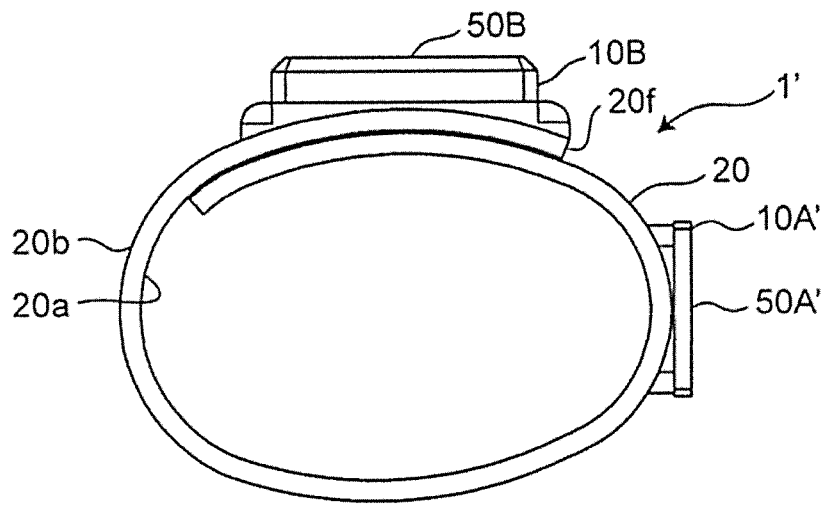
FIG. 24(D) is a front view of the appliance shown in FIG. 24(A).
Figure 24E:
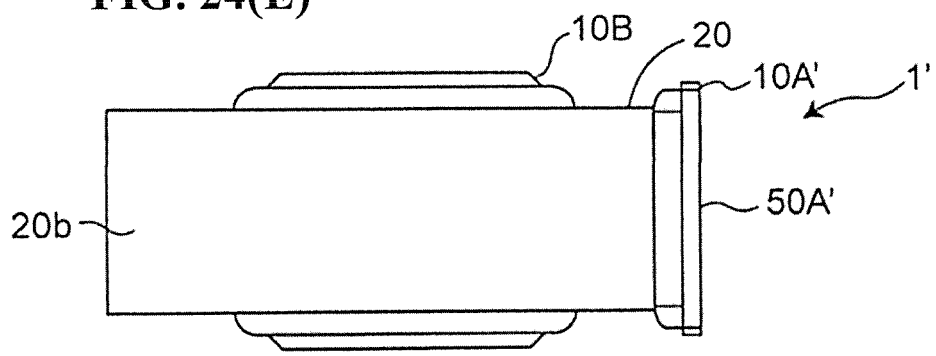
FIG. 24(E) is a bottom view of the appliance shown in FIG. 24(A).

FIG. 24(A) shows an external appearance of the appliance 1' as viewed obliquely. FIG. 24(B), FIG. 24(C), FIG. 24(D), and FIG. 24(E) are a right side view, a top view, a front view, and a bottom view of the appliance 1' shown in FIG. 24(A), respectively.

As shown in the diagrams, the appliance 1' has the same configuration as the appliance 1 described above and performs operation in the same manner as the appliance 1, except that the first display device 50A' (and the main body 10A') is positioned so as to correspond to the radius-side surface 90c of the left wrist 90.

When the user takes the recommended blood pressure measurement posture with the appliance 1' being attached to the left wrist 90 of the user by the belt 20, the first display device 50A' enters the user's field of view. Accordingly, with the appliance 1', as with the appliance 1, it is possible to prompt the user to take the recommended blood pressure measurement posture during a blood pressure measurement period. On the other hand, during a period other than the blood pressure measurement period, the first display device 50A' and the second display device 50B are used to implement a plurality of functions including the blood pressure measurement function.

The embodiment described above is configured such that the output from the acceleration sensor 34 is used to detect the posture of the left wrist 90 of the user and to detect which of the left wrist and the right wrist the appliance 1 is attached to. However, the configuration is not limited thereto. The posture of the left wrist 90 of the user as well as which of the left wrist and the right wrist the appliance 1 is attached to may be detected by using an angular velocity sensor, a barometer sensor, or the like instead of or in addition to the acceleration sensor 34.

Also, the embodiment described above is configured such that the posture guidance information and the worn wrist guidance information are informed to the user by using the display devices 50A and 50B, but the configuration is not limited thereto. It is also possible to inform the user of the posture guidance information and the worn wrist guidance information by using, for example, a sound emitting unit (for example, a beeper) or a vibrator incorporated in the main body 10A or the main body 10B, instead of or in addition to the indications displayed on the display devices 50A and 50B. In this example, a sound emitting unit 54 and a vibrator 55 provided within the main body 10B are indicated by dotted-line blocks in FIG. 3.

For example, with respect to the posture guidance information, control is performed so as to cause the sound emitting unit 54 to emit a sound or the vibrator 55 to vibrate if the posture of the left wrist 90 of the user is out of the recommended blood pressure measurement posture, and to stop the sound emitted from the sound emitting unit 54 or the vibration of the vibrator 55 if the posture of the left wrist 90 of the user matches the recommended blood pressure measurement posture. With this configuration, the user is prompted to bring the posture of the left wrist 90 to match the recommended blood pressure measurement posture in order to stop the sound emitted from the sound emitting unit 54 or the vibration of the vibrator 55. Instead of the above-described control, control may be performed so as to increase the intermittent cycle of emission of the sound from the sound emitting unit 54 or the vibration of the vibrator 55 if the posture of the left wrist 90 of the user is brought away from the recommended blood pressure measurement posture, and to shorten the intermittent cycle of emission of the sound from the sound emitting unit 54 or the vibration of the vibrator 55 if the posture of the left wrist 90 of the user is brought closer to the recommended blood pressure measurement posture. With this configuration, the user is prompted to bring the posture of the left wrist 90 to match the recommended blood pressure measurement posture in order to shorten the intermittent cycle of emission of the sound from the sound emitting unit 54 or the vibration of the vibrator 55.

Also, with respect to the worn wrist guidance information, control is performed so as to cause the sound emitting unit 54 to emit a sound or the vibrator 55 to vibrate if the wrist to which the appliance 1 is attached is the right wrist (unintended wrist), and to stop the sound from the sound emitting unit 54 or the vibration of the vibrator 55 if the wrist to which the appliance 1 is attached is the left wrist (intended wrist). With this configuration, the user is prompted to attach the appliance 1 to the intended wrist in order to stop the sound from the sound emitting unit 54 or the vibration of the vibrator 55.

Also, in the embodiment described above, the appliances 1 and 1' are configured with the intention of being worn around the left wrist 90. However, the configuration is not limited thereto. It is also possible to make an appliance intended to be worn around the right wrist by, for example, modifying the appliance 1 to 1' to have a mirror symmetric outer shape. Such an appliance is useful for a left-handed user.

Also, in the embodiment described above, the first display device serving as the first display region and the second display device serving as the second display region are configured as separate members. However, the configuration is not limited thereto. For example, the first display region and the second display region may be two mutually different regions of one display device that continuously extends in the circumferential direction of the wrist.

Also, in the embodiment described above, a configuration is used in which, in order to implement the blood pressure measurement function, the belt 20 is internally provided with a fluid bladder 21 for compressing the wrist (see FIG. 3) so as to measure blood pressures by an oscillometric method. However, the configuration is not limited thereto. It is also possible to use a configuration in which, for example, a semiconductor sensor array including a plurality of pressure sensors (piezoelectric elements) arranged in an array is provided on the inner circumferential surface of the belt 20 so as to measure blood pressures by a tonometry method (in which blood pressures are measured in a noninvasive manner by pressing the arteries running through the wrist such that a part of the whole circumference of the blood vessels is flat so as to achieve a balance between intra-arterial pressure and extra-arterial pressure). That is, with the appliance according to one or more embodiments of the present invention, it is sufficient that with respect to the blood pressure measurement function, blood pressure measurement can be taken by using the belt 20 wound around the wrist, and thus various configurations and methods can be used in order to implement the blood pressure measurement function.

Also, in the embodiment described above, the "recommended blood pressure measurement posture" is defined as, typically, a posture as shown in FIG. 6 in which the arm is bent and the elbow is rested on a table, with the left wrist 90 being directed obliquely upward and forward and the volar-side surface 90a of the left wrist 90 facing upward. However, the configuration is not limited thereto. The "recommended blood pressure measurement posture" may be a posture in which the forearm is raised so as to intersect obliquely with respect to the trunk in front (the hand pointing upward and the elbow pointing downward), with the left wrist 90 being maintained at the height level of the heart 91 and the radius-side surface c of the left wrist 90 facing upward. The latter posture is preferable particularly when the appliance 1' is used because the user can easily view the first display device 50A'.

The above-described embodiments are merely examples, and various modifications are possible without departing from the scope of the present invention. Also, the multiple above-described embodiments can be achieved independently or in combination with each other. Also, the various characteristics of different embodiments can be achieved independently or in combination with each other.

REFERENCE NUMERALS LIST

1, 1' Appliance
10A, 10A % 10B Main body
20 Belt
50A, 50A' First display device
50B Second display device
52A First operation unit
52B Second operation unit

The invention claimed is:

1. An appliance having a plurality of functions including a blood pressure measurement function and including a belt that is configured to be worn around a wrist of a user, the appliance comprising:
   a fluid bladder disposed in the belt;
   an acceleration sensor configured to produce an acceleration signal representing an acceleration of the belt;
   a first main body comprising a first display region that is positioned in an area of the belt that corresponds to a volar-side surface or a radius-side surface of the wrist; and
   a second main body comprising:
      a second display region that is positioned in an area of the belt that corresponds to a back-side surface of the wrist;
      a pump configured to supply air to the fluid bladder;
      a pump driving circuit configured to drive the pump; and
      a pressure sensor configured to detect pressure in the fluid bladder,
   wherein the second main body is larger in size than the first main body,
   wherein the appliance includes a control unit that detects, based on the acceleration signal, whether or not a posture of the wrist is within an acceptable range of a recommended blood pressure measurement posture, and performs a first control, upon detection that the wrist is within an acceptable range of a recommended blood pressure measurement posture, for setting the first display region in a display mode for displaying a blood pressure measurement information only on the first display region and for setting the second display region in a non-display mode, and further performs blood pressure measurement,
   wherein the information that needs to be displayed includes at least blood pressure values obtained through the blood pressure measurement, and
   wherein, when the user wearing the appliance looks into the first display region, a wrist posture of the wrist to which the appliance is attached matches a recommended blood pressure measurement posture and is correct for the blood pressure measurement.

2. The appliance according to claim 1, wherein an operation unit for inputting an instruction to start the blood pressure measurement period is positioned in the area of the belt that corresponds to the volar-side surface or the radius-side surface of the wrist.

3. The appliance according to claim 2, further comprising:
a starting unit that makes a transition to a start mode in which a preparation for starting the blood pressure measurement period is performed:
if the wrist posture of the wrist to which the appliance is attached is detected and the wrist posture matches the recommended blood pressure measurement posture, and
if an instruction to perform the preparation for starting the blood pressure measurement period is input via the operation unit.

4. The appliance according to claim 3, wherein the starting unit makes a transition to the start mode if the wrist posture is brought within a pre-set first acceptable range of the recommended blood pressure measurement posture, and ends the start mode and starts the blood pressure measurement period if the wrist posture is brought within a pre-set second acceptable range during the start mode, the pre-set second acceptable range being a range that is set to be within the first acceptable range of the recommended blood pressure measurement posture.

5. The appliance according to claim 3, wherein during the start mode, the control unit performs third control for displaying inquiry information for inquiring whether or not to start the blood pressure measurement period only on the first display region.

6. The appliance according to claim 5, wherein the control unit ends the start mode and starts the blood pressure measurement period if an instruction to start the blood pressure measurement period is input via the operation unit after the control unit has displayed the inquiry information on the first display region.

7. The appliance according to claim 1, wherein the control unit performs fourth control for displaying posture guidance information for guiding a user to bring the wrist posture of the wrist to which the appliance is attached so as to match the recommended blood pressure measurement posture on the first or second display region even during the blood pressure measurement period.

8. The appliance according to claim 1, wherein if it is determined, as a result of detection as to which of a left wrist and a right wrist the appliance is attached to, that the appliance is attached to one of the left wrist and the right wrist, the control unit performs fifth control for displaying worn wrist guidance information for guiding a user to detach the appliance from the one of the left wrist and the right wrist and then attach the appliance to another wrist of the left wrist and the right wrist on the first or second display region even during the blood pressure measurement period.

9. The appliance according to claim 7, wherein the control unit displays the posture guidance information on the first or second display region by using an image including a hand or a wrist, or by illuminating or blinking light.

10. The appliance according to claim 8, wherein the control unit displays the worn wrist guidance information on the first or second display region by using an image including a hand or a wrist, or by illuminating or blinking light.

11. The appliance according to claim 1, further comprising:
a sound emitting unit that emits a sound or a vibrator that vibrates,
wherein the control unit informs a user of posture guidance information for guiding the user to bring the wrist posture of the wrist to which the appliance is attached so as to match the recommended blood pressure measurement posture by using the sound from the sound emitting unit or the vibration of the vibrator.

12. The appliance according to claim 1, further comprising:
a sound emitting unit that emits a sound or a vibrator that vibrates,
wherein if it is determined, as a result of detection as to which of a left wrist and a right wrist the appliance is attached to, that the appliance is attached to one of the left wrist or the right wrist, the control unit informs a user of worn wrist guidance information for guiding the user to detach the appliance from the one of the left wrist and the right wrist and then attach the appliance to another wrist of the left wrist and the right wrist by using the sound from the sound emitting unit or the vibration of the vibrator.

13. The appliance according to claim 1, further comprising:
a first operation unit for inputting an instruction to perform a function of the appliance, the first operation unit being positioned in the area of the belt that corresponds to the volar-side surface or the radius-side surface of the wrist; and
a second operation unit for inputting an instruction to perform a function of the appliance, the second operation unit being positioned in the area of the belt that corresponds to the back-side surface of the wrist,
wherein an instruction to start the blood pressure measurement period can be input only via the first operation unit among the first and second operation units.

14. The appliance according to claim 4, wherein during the start mode, the control unit performs third control for displaying inquiry information for inquiring whether or not to start the blood pressure measurement period only on the first display region.

15. The appliance according to claim 5, wherein the control unit performs fourth control for displaying posture guidance information for guiding a user to bring the wrist posture of the wrist to which the appliance is attached so as to match the recommended blood pressure measurement posture on the first or second display region even during the blood pressure measurement period.

16. The appliance according to claim 6, wherein the control unit performs fourth control for displaying posture guidance information for guiding a user to bring the wrist posture of the wrist to which the appliance is attached so as to match a recommended blood pressure measurement posture on the first or second display region even during the blood pressure measurement period.

17. The appliance according to claim 7, wherein if it is determined, as a result of detection as to which of a left wrist and a right wrist the appliance is attached to, that the appliance is attached to one of the left wrist or the right wrist, the control unit performs fifth control for displaying worn wrist guidance information for guiding a user to detach the appliance from the one of the left wrist and the right wrist and then attach the appliance to another wrist of the left wrist and the right wrist on the first or second display region even during the blood pressure measurement period.

18. The appliance according to claim 15, wherein if it is determined, as a result of detection as to which of a left wrist and a right wrist the appliance is attached to, that the appliance is attached to one of the left wrist or the right wrist, the control unit performs fifth control for displaying worn wrist guidance information for guiding a user to detach the appliance from the one of the left wrist or the right wrist and then attach the appliance to another wrist of the left wrist and the right wrist on the first or second display region even during the blood pressure measurement period.

19. The appliance according to claim 16, wherein if it is determined, as a result of detection as to which of a left wrist and a right wrist the appliance is attached to, that the appliance is attached to one of the left wrist and the right wrist, the control unit performs fifth control for displaying worn wrist guidance information for guiding a user to detach the appliance from the one of the left wrist and the right wrist and then attach the appliance to another wrist of the left wrist and the right wrist on the first or second display region even during the blood pressure measurement period.

20. The appliance according to claim 1, wherein the acceleration sensor is used to determine whether the wrist posture, including an angular position of the volar-side surface about the wrist, matches the recommended blood pressure measurement posture.

21. The appliance according to claim 1, wherein the appliance performs second control for displaying information that needs to be displayed at least on the second display region during a period other than the blood pressure measurement period.

* * * * *